US012655184B2

(12) United States Patent
Radosevich et al.

(10) Patent No.: US 12,655,184 B2
(45) Date of Patent: Jun. 16, 2026

(54) LABYRINTHIN-BASED PEPTIDES FOR CANCER IMMUNOTHERAPIES AND USES THEREOF

(71) Applicant: LABYRX IMMUNOLOGIC THERAPEUTICS (USA) LIMITED, Auburn, CA (US)

(72) Inventors: James A. Radosevich, Belvidere, IL (US); Michael Babich, Auburn, CA (US)

(73) Assignee: Labyrx Immunologic Therapeutics (USA) Limited, Auburn, CA (US)

( * ) Notice: Subject to any disclaimer, the term of this patent is extended or adjusted under 35 U.S.C. 154(b) by 1052 days.

(21) Appl. No.: 17/309,648

(22) PCT Filed: Dec. 13, 2019

(86) PCT No.: PCT/US2019/066264
§ 371 (c)(1),
(2) Date: Jun. 11, 2021

(87) PCT Pub. No.: WO2020/123964
PCT Pub. Date: Jun. 18, 2020

(65) Prior Publication Data
US 2022/0409709 A1 Dec. 29, 2022

Related U.S. Application Data

(60) Provisional application No. 62/779,377, filed on Dec. 13, 2018.

(51) Int. Cl.
*A61K 39/00* (2006.01)
*A61P 35/00* (2006.01)
*C07K 14/47* (2006.01)

(52) U.S. Cl.
CPC .. *C07K 14/4748* (2013.01); *A61K 39/001102* (2018.08); *A61P 35/00* (2018.01)

(58) Field of Classification Search
None
See application file for complete search history.

(56) References Cited

U.S. PATENT DOCUMENTS

| | | | | |
|---|---|---|---|---|
| 6,166,176 A | * | 12/2000 | Radosevich | ....... C07K 14/4748 424/277.1 |
| 6,727,080 B1 | | 4/2004 | Radosevich | |
| 2008/0153737 A1 | | 6/2008 | Lieberman | |
| 2010/0233711 A1 | | 9/2010 | Radosevich | |
| 2011/0110963 A1 | * | 5/2011 | Radosevich | ........... C07H 21/04 530/387.9 |
| 2011/0230433 A1 | | 9/2011 | Loeb | |
| 2015/0274787 A1 | | 10/2015 | Wink | |
| 2018/0142034 A1 | | 5/2018 | Chang | |
| 2020/0190480 A1 | * | 6/2020 | Moshiri | ........... G01N 33/57492 |

FOREIGN PATENT DOCUMENTS

| | | | |
|---|---|---|---|
| JP | 2013116891 A | 6/2013 | |
| WO | 199013564 A1 | 11/1990 | |
| WO | 200789866 A2 | 8/2007 | |
| WO | 2011112906 A2 | 9/2011 | |
| WO | 2016161390 A1 | 10/2016 | |
| WO | 2017147383 A1 | 8/2017 | |
| WO | 2017177337 A1 | 10/2017 | |
| WO | 2018200496 A1 | 11/2018 | |

OTHER PUBLICATIONS

Grandi et al. (Frontiers in Oncology, Oct. 2018, p. 1-14).*
Babich, M. et al. (2002). "Labyrinthin: A Distinct Pan-Adenocarcinoma Diagnostic and Immunotherapeutic Tumor Specific Antigen," Heliyon 8:e08988, 11 pages.
Babich, M. et al. (May 7, 2006) "X509Fab: A Humanized Antibody Against Labyrinthin—An Adenocarcinoma Cell- Specific Target," The FASEB Journal 20(5):LB109-LB109, Abstract Only, 2 pages.
Padilleau-Lefevre, S. et al. (Mar. 2007). "Expression and Detection Strategies for an scFv Fragment Retaining the Sam High Affinity Than Fab and Whole Antibody: Implications for Therapeutics Use in Prion Diseases," Molecular Immunology 44(8):1888-1896.
Clarke, S.C. et al. (Jan. 7, 2019). "Multispecific Antiibody Development Platform Based on Human Chain Antibodies," Front. Immunol. 9(3037):1-13.
Edwards, B.M. et al. (Nov. 14, 2003). "The Remarkable Flexibility of the Human Antibody Repertoire; Isolation of Over One Thousand Different Antibodies to a Single Protein, BLyS," J. Mol. Biol. 334(1):103-118.
Hinrichs, C.S. et al. (Jan. 2014). "Exploiting the Curative Potential of Adoptive T-Cell Therapy for Cancer," 257(1):56-71, 23 pages.
June, C.H. et al. (Jul. 5, 2018). "Chimeric Antigen Receptor Therapy," N. Engl. J. Med. 379(1):64-73, 15 pages.
Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3):159-168.
Saleev, N. et al. (Jul. 1, 2019). "Abstract 2297: Anti-Labryinthin Monoclonal Antibody Reduces Human Adenocarcinoma Circulating Tumor Cells in the Blood of Patient-Derived Xenograft Models and Inhibits the Growth of Adenocarcinoma Cell Cultures," Cancer Research 79(13):2297, 4 pages.

* cited by examiner

*Primary Examiner* — Agnieszka Boesen
(74) *Attorney, Agent, or Firm* — MORRISON & POERSTER LLP

(57) ABSTRACT

Antigenic compositions comprising one or more labyrinthin-derived peptides are described herein. In some embodiment, each peptide of the antigenic composition comprises a T-cell epitope and/or a B-cell epitope. In other aspects, the present disclosure provides, e.g., vaccine compositions comprising tin antigenic composition disclosed herein, including kits, medicines, and compositions (such as pharmaceutical compositions and unit dosages) thereof. Also provided are methods of using the compositions disclosed herein, such as methods of treatment thereof and methods of producing antibodies, and antibody compositions thereof, against the one or more labyrinthin-derived peptides or a portion thereof.

1 Claim, 6 Drawing Sheets

Specification includes a Sequence Listing.

LABYRINTHIN-BASED PEPTIDES FOR CANCER IMMUNOTHERAPIES AND USES THEREOF

CROSS-REFERENCE TO RELATED APPLICATIONS

This application is the national stage application under 35 U.S.C. § of International Application No. PCT/US2019/066264, filed on Dec. 13, 2019, which claims priority to U.S. Provisional Patent Application No. 62/779,377, filed on Dec. 13, 2018, the disclosure of each of which is hereby incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 185722000100SeqList.TXT, date recorded: Jun. 11, 2021, size: 8 KB).

TECHNICAL FIELD

In some aspects, the present application relates to antigenic compositions comprising one or more labyrinthin-derived peptides. In other aspects, the present application relates to antigenic compositions comprising one or more labyrinthin-derived peptides, wherein each peptide comprises a T-cell epitope and/or a B-cell epitope. In other aspects, the present application relates to antibodies produce by vaccinating a subject with the compositions disclosed herein.

BACKGROUND

Historically, cancer has been characterized largely based on the tissue type or organ in which the cancer originates, e.g., lung cancer, breast cancer, and colon cancer. Many cancer treatments are also based on the tissue or organ-based classification of the cancer. It is well recognized that such tissue or organ-based classification of cancers may not provide sufficient guidance for selection of an efficacious treatment. This is due, in part, to the finding that cancers originating from a single tissue type or organ may be highly heterogeneous, and such differences may require a person-alized cancer treatment approach. For example, defining cancers by a biomarker, as opposed to a tissue type or organ of origin, may allow for improved cancer treatment, e.g., triple negative breast cancer, which lacks expression of estrogen receptors, progesterone receptors, and HER2/neu, is not responsive to traditional hormone-based therapies that target any one or more of the identified receptors and requires alternative treatments. After identification of a cancer subtype based on a biomarker, significant research is required to develop novel agents for efficacious treatment of such a cancer subtype.

One such identified cancer subtype is a labyrinthin-expressing cancer. Labyrinthin is a cell surface protein expressed on the extracellular surface of the plasma membrane of some cancers, such as adenocarcinomas. Cell surface expression of labyrinthin is not cell cycle specific. Furthermore, labyrinthin is not found in the serum of normal or tumor bearing patients, and is not shed into the culture media by labyrinthin positive cell lines. Thus, labyrinthin represents a useful marker for defining a subtype of cancer, namely, labyrinthin-expressing cancer.

Cancer vaccines targeting labyrinthin-expressing cancers via only B-cell-mediated adaptive immune system antibody production have been disclosed. See U.S. Pat. Nos. 6,166, 176 and 7,635,759, which are hereby incorporated by reference in their entirety.

All references cited herein, including patent applications and publications, are incorporated by reference in their entirety.

BRIEF SUMMARY

In one aspect, the present application provides antigenic compositions comprising one or more labyrinthin-derived peptides. In some embodiments, the present application provides antigenic compositions comprising one or more labyrinthin-derived peptides, wherein each labyrinthin-derived peptide comprises one or more of a T-cell epitope and a B-cell epitope. In some embodiments, each of the one or more labyrinthin-derived peptides comprises a T-cell epitope and a B-cell epitope. In some embodiments, the one or more labyrinthin-derived peptides are between 8 and 25 amino acids in length. In some embodiments, the one or more labyrinthin-derived peptides are substantially homologous to a portion of labyrinthin. In some embodiments, each of the one or more labyrinthin-derived peptides comprises a non-terminal proline residue.

In another aspect, the present application provides antigenic compositions comprising one or more labyrinthin-derived peptides selected from the group consisting of: (a) a first peptide comprising SEQ ID NO:25 or a variant thereof; (b) a second peptide comprising SEQ ID NO:26 or a variant thereof; (c) a third peptide comprising SEQ ID NO:27 or a variant thereof; and (d) a fourth peptide comprising SEQ ID NO:28 or a variant thereof, wherein the one or more labyrinthin-derived peptides are between 12 and 25 amino acids in length, and wherein each peptide comprises a T-cell epitope and a B-cell epitope. In some embodiments, the first peptide comprises SEQ ID NO:25. In some embodiments, the second peptide comprises SEQ ID NO:26. In some embodiments, the third peptide comprises SEQ ID NO:27. In some embodiments, the fourth peptide comprises SEQ ID NO:28.

In some embodiments, the one or more labyrinthin-derived peptides are between 21 and 24 amino acids in length. In some embodiments, the one or more labyrinthin-derived peptides are 22 or 23 amino acids in length.

In some embodiments, the one or more labyrinthin-derived peptides are substantially homologous to a portion of labyrinthin.

In some embodiments, the first peptide is SEQ ID NO:29 or a variant thereof having 1 or 2 amino acids substituted, deleted, inserted, and/or added relative to SEQ ID NO:29. In some embodiments, the first peptide is SEQ ID NO:29.

In some embodiments, the second peptide is SEQ ID NO:30 or a variant thereof having 1 or 2 amino acids substituted, deleted, inserted, and/or added relative to SEQ ID NO:30. In some embodiments, the second peptide is SEQ ID NO:30.

In some embodiments, the third peptide is SEQ ID NO:31 or a variant thereof having 1 or 2 amino acids substituted, deleted, inserted, and/or added relative to SEQ ID NO:31. In some embodiments, the third peptide is SEQ ID NO:31.

In some embodiments, the fourth peptide is SEQ ID NO:32 or a variant thereof having 1 or 2 amino acids substituted, deleted, inserted, and/or added relative to SEQ ID NO:32. In some embodiments, the fourth peptide is SEQ ID NO:32.

In some embodiments, at least one of the one or more labyrinthin-derived peptides is conjugated to a linker.

In some embodiments, the antigenic composition comprises two or more of the labyrinthin-derived peptides. In some embodiments, the antigenic composition comprises three or more of the labyrinthin-derived peptides. In some embodiments, the antigenic composition comprises four of the labyrinthin-derived peptides.

In another aspect, the present application provides nucleic acid compositions comprising one or more nucleic acids encoding at least one of the one or more labyrinthin-derived peptides comprised in the antigenic compositions described herein.

In another aspect, the present application provides vaccine compositions comprising: (a) an effective amount of the antigenic compositions described herein; and (b) a pharmaceutically acceptable vehicle. In some embodiments, the pharmaceutically acceptable vehicle is selected from the group consisting of an aqueous suspension, an oily suspension, an emulsion, a liposome, a virosome, and a nanoparticle. In some embodiments, the pharmaceutically acceptable vehicle comprises an excipient. In some embodiments, the pharmaceutically acceptable vehicle comprises an adjuvant. In some embodiments, the adjuvant is an immune-enhancing adjuvant.

In another aspect, the present application provides methods for treating a cancer in an individual in need thereof, the method comprising administering to the individual a vaccine composition described herein. In some embodiments, the method further comprises administering to the individual an immune checkpoint inhibitor.

In another aspect, the present application provides methods of producing an antibody in a host animal, the method comprising administering to the host animal an antigenic composition described herein, a nucleic acid composition described herein, or a vaccine composition described herein, thereby producing the antibody.

DETAILED DESCRIPTION

Figure 1A:
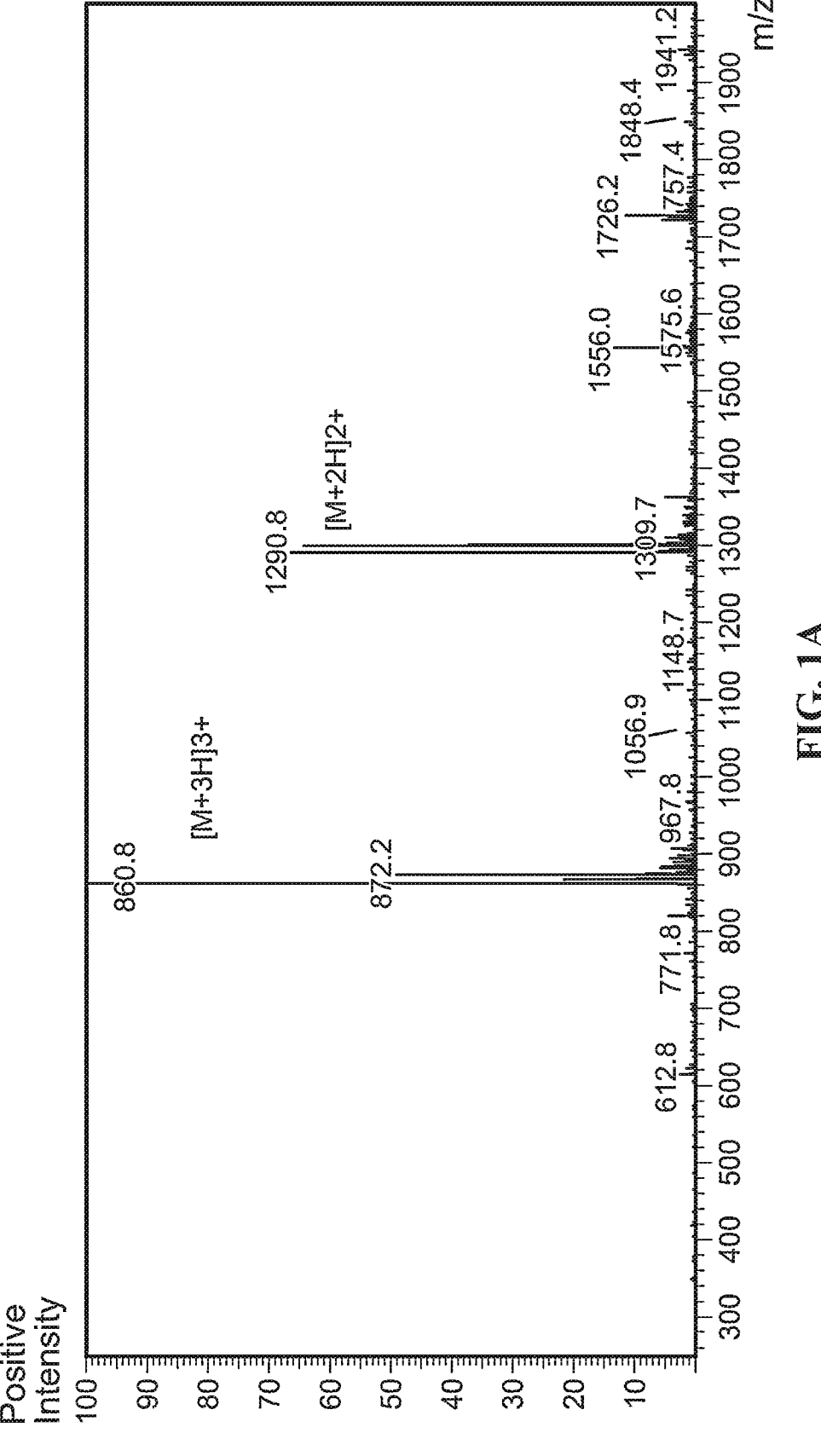
FIGS. 1A-1D each show a mass spectrum of the parent ion m/z of a labyrinthin-derived peptide candidate.
Figure 1B:
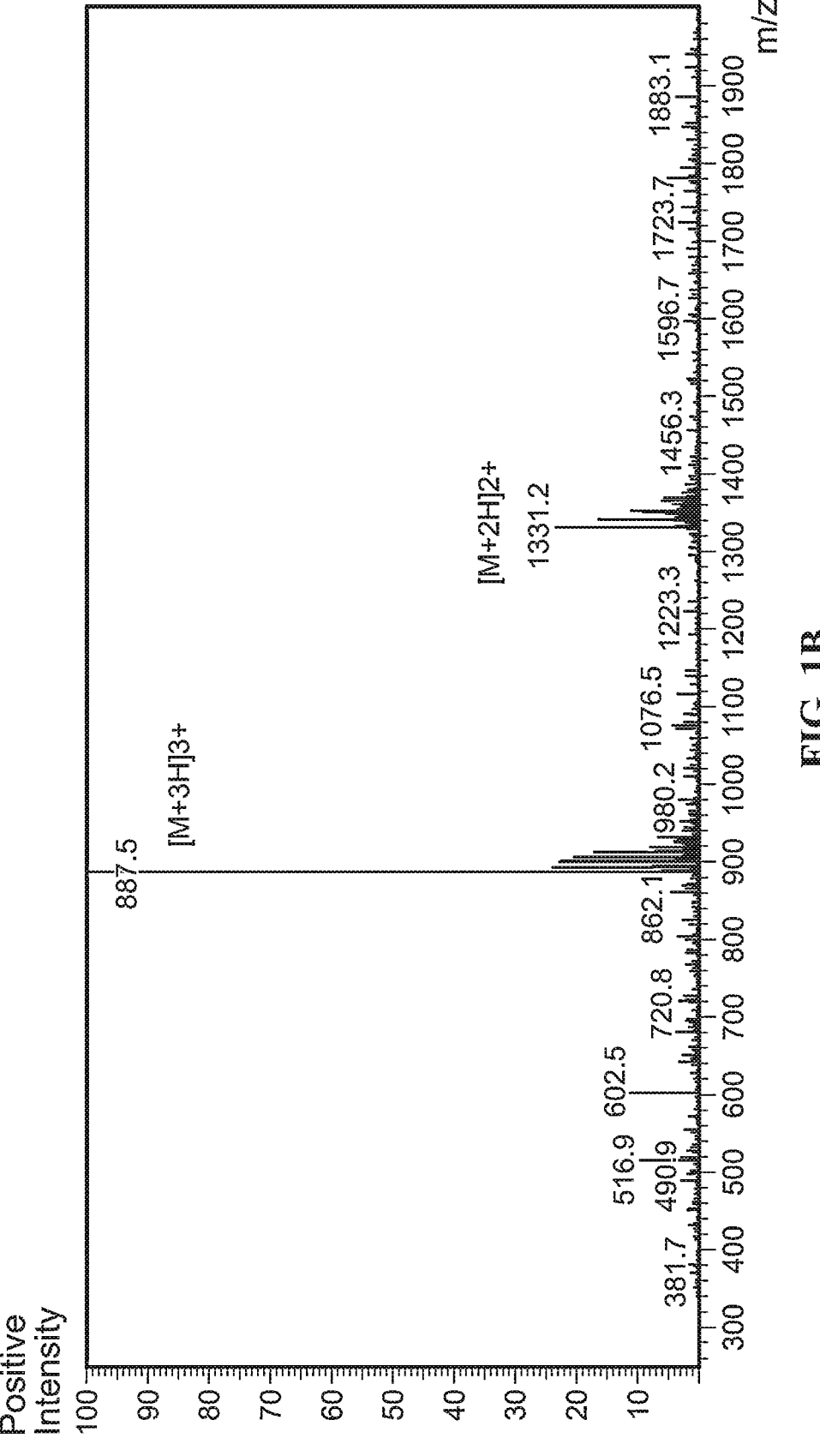
Figure 1C:
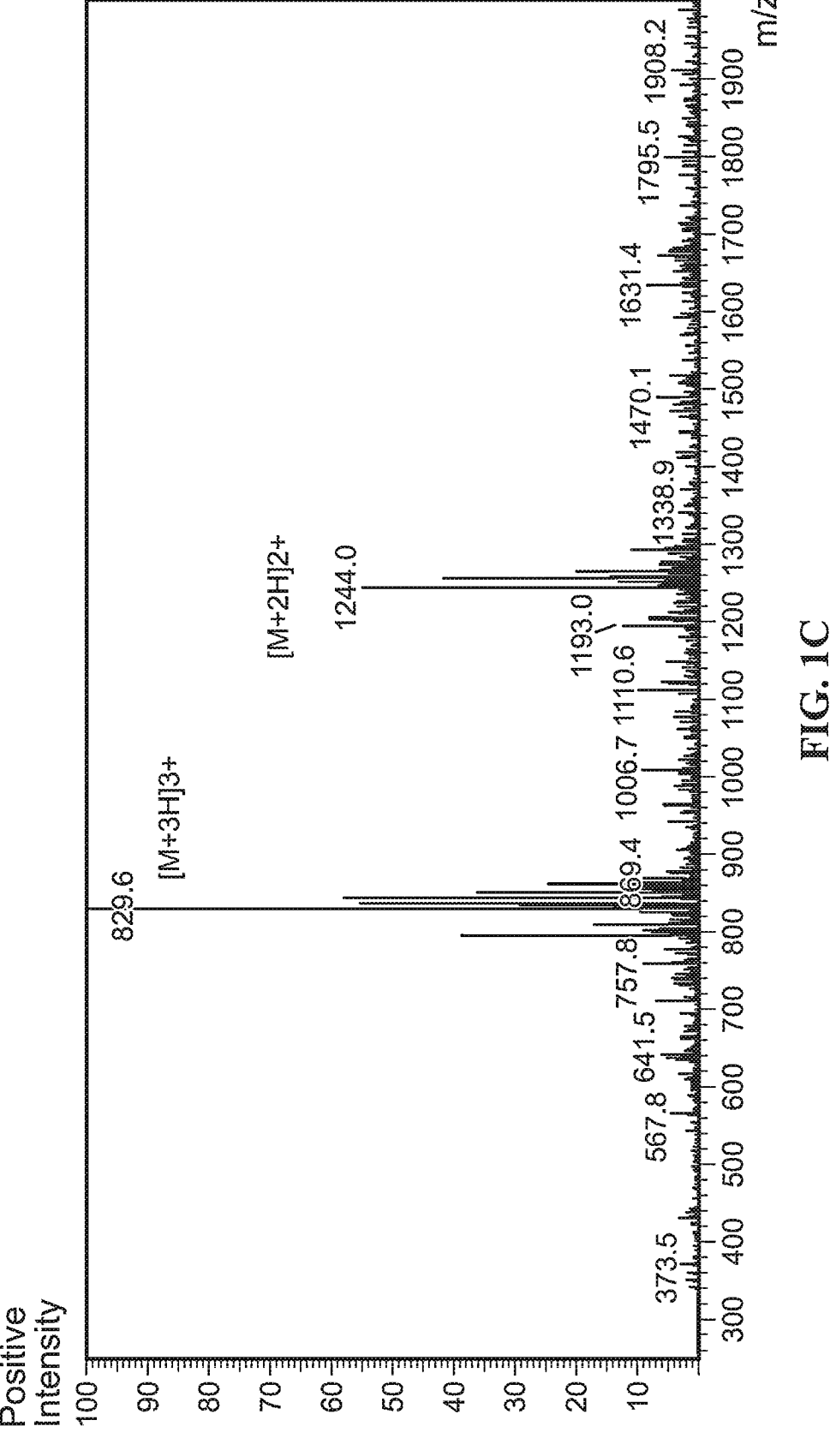
Figure 1D:
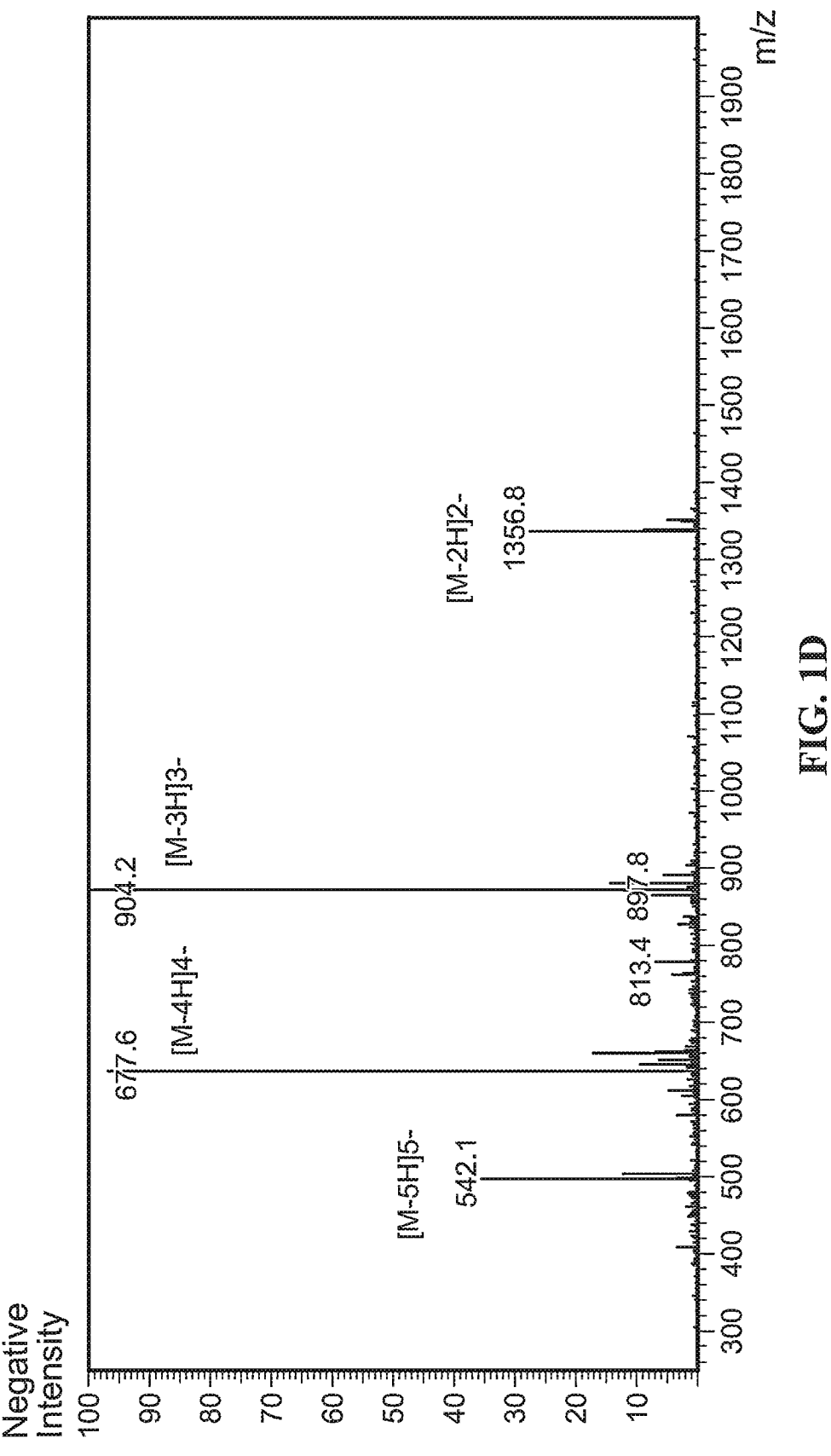

The present application provides, in some aspects, an antigenic composition comprising one or more labyrinthin-derived peptides. In some embodiments, the labyrinthin-derived peptide comprises a T-cell epitope. In some embodiments, the labyrinthin-derived peptide comprises a B-cell epitope. In some embodiments, the labyrinthin-derived peptide comprises a B-cell and a T-cell epitope. In some embodiments, the labyrinthin-derived peptide activates T-cell and B-cell adaptive immune responses. In some embodiments, the one or more labyrinthin-derived peptides are between 8 and 25 amino acids in length, such as between 12 and 25 amino acids in length.

The disclosure of the present application is based, in part, on the finding that a labyrinthin-derived peptide can be designed to comprise a B-cell epitope and/or a T-cell epitope to trigger a B-cell-mediated adaptive immune response and also elicit a T-cell-mediated adaptive immune response to more effectively destroy cancer cells. In some aspects, the disclosure of the present application is based, in part, on the finding that a labyrinthin-derived peptide can be designed to elicit an immune response to effectively destroy cancer cells. Vaccines comprising such labyrinthin-derived peptides, and combinations comprising one or more of such labyrinthin-derived peptides, will allow for improved treatments of labyrinthin-expressing cancers.

Design of a labyrinthin-derived peptide that comprises a B-cell epitope and a T-cell epitope is challenging as mechanisms of antigen recognition differ greatly between B-cells and T-cells. B-cells, via antigen receptors comprising immunoglobulins, target solvent-exposed antigens, including both linear and conformational antigens. In contrast, T-cells, via T-cell receptors, recognize antigens presented on the surface of antigen-presenting cells (APCs). Such antigens are processed by an APC and then presented on the surface of the APC by, e.g., class I major histocompatibility complexes (MHCI) or class II major histocompatibility complexes (MHCII). See, e.g., Sanchez-Trincado, J. L., et al., *J Immunol*, 2017.

In vivo antigen recognition by B-cells and T-cells is highly unpredictable. Increasing peptide antigen length increases cross-reactivity with non-target antigens. Thus, it is a challenge to create peptides that activate B-cell and T-cell immune responses with high target specificity, which can be synthesized and stably formulated in a pharmaceutically acceptable vehicle, are safe for in vivo use, and raise enough of an immunogenic response to be efficacious in the treatment of cancer. The present application discloses labyrinthin-derived peptides that comprise a B-cell epitope and a T-cell epitope and are suitable for use in a cancer vaccine.

Thus, the disclosure provides, in some aspects, antigenic compositions comprising one or more labyrinthin-derived peptides, wherein each labyrinthin-derived peptide comprises one or more of a T-cell epitope and a B-cell epitope. In some embodiments, each of the one or more labyrinthin-derived peptides comprises a T-cell epitope and a B-cell epitope. In some embodiments, the one or more labyrinthin-derived peptides are between 8 and 25 amino acids in length. In some embodiments, the one or more labyrinthin-derived peptides are substantially homologous to a portion of labyrinthin. In some embodiments, each of the one or more labyrinthin-derived peptides comprises a non-terminal proline residue.

In other aspects, the present disclosure provides antigenic compositions comprising one or more labyrinthin-derived peptides selected from the group comprising: (a) a first peptide comprising SEQ ID NO:25 or a variant thereof, (b) a second peptide comprising SEQ ID NO:26 or a variant thereof; (c) a third peptide comprising SEQ ID NO:27 or a variant thereof, and (d) a fourth peptide comprising SEQ ID NO:28 or a variant thereof, wherein the one or more labyrinthin-derived peptides are between 12 and 25 amino acids in length, and wherein each peptide comprises a T-cell epitope and a B-cell epitope. In some embodiments, the one or more labyrinthin-derived peptides comprise two or more labyrinthin-derived peptides. In some embodiments, the one or more labyrinthin-derived peptides comprise three or more labyrinthin-derived peptides. In some embodiments, the one or more labyrinthin-derived peptides comprise four labyrinthin-derived peptides. Also provided are compositions comprising an antigenic composition disclosed herein, including kits, medicines, and compositions (such as pharmaceutical compositions and unit dosages) thereof.

In other aspects, the present disclosure provides vaccine compositions comprising: (a) an antigenic composition disclosed herein; and (b) a pharmaceutically acceptable vehicle. Also provided are vaccine compositions comprising an antigenic composition disclosed herein, including kits, medicines, and compositions (such as pharmaceutical compositions and unit dosages) thereof.

In other aspects, the present disclosure provides methods for treating a cancer in an individual in need thereof, the methods comprising administering to the individual a vaccine composition described herein.

In other aspects, the present disclosure provides methods of producing an antibody in a host animal, the methods comprising administering to the host animal any of an antigenic composition, a nucleic acid, or a vaccine composition described herein, thereby producing the antibody.

It will also be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects.

Definitions

The term "substantially homologous," as used herein, refers to the sequence similarity of a sequence disclosed herein as compared to a reference sequence, wherein the sequence has at least about 85% similarity (e.g., homology) with a reference or a portion thereof, such as at least about any of 86% similarity, 87% similarity, 88% similarity, 89% similarity, 90% similarity, 91% similarity, 92% similarity, 93% similarity, 94% similarity, 95% similarity, 96% similarity, 97% similarity, 98% similarity, 99% similarity, or 100% similarity. Methods for determining sequence similarity are known in the art, e.g., as described in Pearson, W. R., *Curr Protoc Bioinformatics,* 2013.

The term "treating" or "treatment," as used herein, is an approach for obtaining beneficial or desired results including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (e.g., partial or total) of the disease, decreasing the dose of one or more other medications required to treat the disease, delaying the progression of the disease, increasing the quality of life, and/or prolonging survival. Also encompassed by "treating" or "treatment" is a reduction of pathological consequence of the cancer. The methods of the present application contemplate any one or more of these aspects of treatment.

The term "combination therapy" or "combination treatment," as used herein, is meant that a first agent be administered in conjunction with at least one other agent. "In conjunction with" refers to administration of one treatment modality, such as a vaccine composition, in addition to, but not necessarily at the same time as, administration of another treatment modality. As such, "in conjunction with" refers to administration of one treatment modality before, during, or after delivery of the other treatment modality to the individual.

The term "effective amount," as used herein, refers to an amount of a compound or composition sufficient to treat a specified disorder, condition, or disease, such as ameliorate, palliate, lessen, and/or delay one or more symptoms of the disorder, condition, or disease. In reference to cancer, an effective amount comprises an amount sufficient to, e.g., cause a tumor to shrink and/or to decrease the growth rate of the tumor (such as to suppress tumor growth) or to prevent or delay other unwanted cell proliferation in the cancer. In some embodiments, an effective amount is an amount sufficient to delay development of cancer. In some embodiments, an effective amount is an amount sufficient to prevent or delay recurrence. An effective amount can be administered in one or more administrations. In the case of cancer, the effective amount of the drug or composition may: (i) reduce the number of cancerous cells; (ii) reduce tumor size; (iii) inhibit, retard, slow to some extent and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "simultaneous administration" or equivalents thereof, as used herein, means that a first therapy and second therapy in a combination therapy are administered with a time separation of no more than about 15 minutes, such as no more than about any of 10 minutes, 5 minutes, or 1 minute. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

The term "sequential administration" or equivalents thereof, as used herein, means that the first therapy and second therapy in a combination therapy are administered with a time separation of more than about 15 minutes, such as more than about any of 20 minutes, 30 minutes, 40 minutes, 50 minutes, or 60 minutes. The methods disclosed herein encompass scenarios wherein either a first therapy or a second therapy may be administered first. The first and second therapies generally will be contained in separate compositions, which may be contained in the same or different packages or kits.

The term "concurrent administration" or equivalents thereof, as used herein, means that the administration of a first therapy and the administration of a second therapy in a combination therapy overlap with one another.

The term "individual" refers to a mammal and includes, but is not limited to, human, bovine, horse, feline, canine, rodent, or primate.

As used herein, "delaying" the development of cancer means to defer, hinder, slow, retard, stabilize, and/or postpone development of the disease. This delay can be of varying lengths of time, depending on the history of the disease and/or individual being treated. As is evident to one of ordinary skill in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "pharmaceutically acceptable" or "pharmacologically compatible," as used herein, is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers, excipients, or salts have preferably met the required standards of toxicological and manufacturing testing and/or are included on the Inactive Ingredient Guide prepared by the U.S. Food and Drug administration.

The term "based on" or "basis for," as used herein, includes assessing, determining, obtaining, or measuring one or more characteristic of an individual or a cancer therein as described herein, and in some embodiments, selecting the individual suitable for receiving a treatment as described in the methods disclosed herein. For example, when a labyrinthin status of a cancer is used as a basis for selecting an individual for a treatment method herein, assessing (or aiding in assessing), measuring, obtaining, or determining the labyrinthin status may be included in a method of a treatment as described herein, e.g., the labyrinthin status is measured before and/or during and/or after treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; or (g) predicting likelihood of clinical benefits.

The basis or bases disclosed herein for use with the methods of the present application, such a labyrinthin status, may, in some aspects, be based on a comparison to a control. In some embodiments, control is a known standard obtained from the literature (e.g., a known gene sequence, RNA sequence, protein sequence, gene expression level). In some embodiments, the control is a control sample obtained from the individual to be, or being, treated using the methods disclosed herein (e.g., a control sample from a non-cancerous tissue). In some embodiments, the control is a control sample obtained from an individual other than the individual to be, or being, treated using the methods disclosed herein (e.g., a control sample from a healthy volunteer or a volunteer not having cancer). In some embodiments, the control is obtained from a given patient population. For example, regarding a level of gene expression or enzyme activity level, a control level may be the median expression level of that gene or the median enzyme activity level of that enzyme for the patient population. And, for example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest. In some embodiments, the single patient has a disease (such as cancer) and the patient population does not have the disease. In some embodiments, the single patient and the patient population have the same histological type of a disease. A population may be about, or alternatively at least about any of the following, in terms of number of individuals measured: 2, 5, 10, 15, 20, 25, 30, 50, 60, 75, 100, 125, 150, 175, 200, 225, 250, 300, 400, 500. Preferably, a sufficient number of individuals are measured to provide a statistically significant population, which can be determined by methods known in the art. In some embodiments, the population is a group participating in a clinical trial.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Antigenic Compositions Comprising a Labyrinthin-Derived Peptide

The present application provides, in some aspects, antigenic compositions comprising one or more labyrinthin-derived peptides. Labyrinthin is a protein having the 255 amino acid sequence recited in SEQ ID NO:1 (as shown in Table 1). Transcriptional variants associated with labyrinthin are known, including junctate, humbug, and human aspartyl beta-hydroxylase (HAAH) (see, e.g., U.S. Pat. No. 6,166, 176, which is hereby incorporated by reference in its entirety).

TABLE 1

| Amino acid sequence of labyrinthin. |
| --- |

Amino acid sequence

SEQ ID  Met-Val-Ile-Ala-Leu-Leu-Gly-Val-Trp-Thr-Ser-Val-Ala-Val-Val-
NO: 1   Trp-Phe-Asp-Leu-Val-Asp-Tyr-Glu-Glu-Val-Leu-Gly-Lys-Leu-Gly-
        Ile-Tyr-Asp-Ala-Asp-Gly-Asp-Gly-Asp-Phe-Asp-Val-Asp-Asp-Ala-
        Lys-Val-Leu-Leu-Gly-Leu-Lys-Glu-Arg-Ser-Thr-Ser-Glu-Pro-Ala-
        Val-Pro-Pro-Glu-Glu-Ala-Glu-Pro-His-Thr-Glu-Pro-Glu-Glu-Gln-
        Val-Pro-Val-Glu-Ala-Glu-Pro-Gln-Asn-Ile-Glu-Asp-Glu-Ala-Lys-
        Glu-Gln-Ile-Gln-Ser-Leu-Leu-His-Glu-Met-Val-His-Ala-Glu-His-
        Val-Glu-Gly-Glu-Asp-Leu-Gln-Gln-Glu-Asp-Gly-Pro-Thr-Gly-Glu-
        Pro-Gln-Gln-Glu-Asp-Asp-Glu-Phe-Leu-Met-Ala-Thr-Asp-Val-Asp-
        Asp-Arg-Phe-Glu-Thr-Leu-Glu-Pro-Glu-Val-Ser-His-Glu-Glu-Thr-
        Glu-His-Ser-Tyr-His-Val-Glu-Glu-Thr-Val-Ser-Gln-Asp-Cys-Asn-
        Gln-Asp-Met-Glu-Glu-Met-Met-Ser-Glu-Gln-Glu-Asn-Pro-Asp-Ser-
        Ser-Glu-Pro-Val-Val-Glu-Asp-Glu-Arg-Leu-His-His-Asp-Thr-Asp-
        Asp-Val-Thr-Tyr-Gln-Val-Tyr-Glu-Glu-Gln-Ala-Val-Tyr-Glu-Pro-
        Leu-Glu-Asn-Glu-Gly-Ile-Glu-Ile-Thr-Glu-Val-Thr-Ala-Pro-Pro-
        Glu-Asp-Asn-Pro-Val-Glu-Asp-Ser-Gln-Val-Ile-Val-Glu-Glu-Val-
        Ser-Ile-Phe-Pro-Val-Glu-Glu-Gln-Gln-Glu-Val-Pro-Pro-Asp-Thr

The antigenic compositions disclosed herein comprise one or more labyrinthin-derived peptides described herein, which are based, in whole or in part, on the sequence of labyrinthin (SEQ ID NO:1). In some embodiments, the antigenic composition comprises a labyrinthin-derived peptide comprising a T-cell epitope and/or a B-cell epitope.

In some embodiments, the antigenic composition comprises at least two, such as at least any of 3, 4, 5, 6, 7, 8, 9, 10, 11, 12, 13, 14, or 15 labyrinthin-derived peptides. In some embodiments, the labyrinthin-derived peptides described herein have one or more of the following properties: can be readily synthesized, such as on a commercial scale, is soluble, such as in an aqueous solution, has a low pI (e.g., less than about 3.6, such as less than about any of 3.4 or 3.3), has a desired charge, such as a low charge, binds to a complex, such as to MHC, is processed by cells for presentation, demonstrates in vivo presentation, and triggers an immune response. Additionally, in some embodiments, the labyrinthin-derived peptides, and compositions thereof such as antigenic compositions and/or vaccine compositions, described herein have freeze-thaw stability, e.g., less than 15% of the labyrinthin-derived peptide is degraded over the course of at least three freeze-thaw cycles. In some embodiments, the labyrinthin-derived peptides, and compositions thereof such as antigenic compositions and/or vaccine compositions, described herein have room temperature stability, e.g., less than 15% of the labyrinthin-derived peptide is degraded over a room temperature incubation of at least 6 hours. In some embodiments, the labyrinthin-derived peptide is a peptide having a sequence similarity of at least about 60% similarity, such as at least about any of 65% similarity, 70% similarity, 75% similarity, 80% similarity, 85% similarity, 90% similarity, or 95% similarity, to a portion of labyrinthin (SEQ ID NO:1), wherein the labyrinthin-derived peptide does not comprise a terminal proline residue, and wherein the labyrinthin-derived peptide comprises at least one proline residue, such as 2, 3, 4, or 5 proline residues. In some embodiments, the labyrinthin-derived peptide is a peptide having a sequence similarity of at least about 60% similarity, such as at least about any of 65% similarity, 70% similarity, 75% similarity, 80% similarity, 85% similarity, 90% similarity, or 95% similarity, to a portion of labyrinthin (SEQ ID NO:1), wherein one terminus of the labyrinthin-derived peptide does not comprise a terminal proline residue, and wherein the labyrinthin-derived peptide comprises at least one proline residue, such as 2, 3, 4, or 5 proline residues. In some embodiments, the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide is 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In some embodiments, the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide or a derivative thereof has a sequence similarity of at least about 60% similarity to a portion of labyrinthin (SEQ ID NO:1), wherein 1, 2, 3, 4, of 5 amino acids of the sequence of the labyrinthin-derived peptide are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker. In some embodiments, the labyrinthin-derived peptide has a pI of between about 3.4 to about 3.1, such as about 3.3 to about 3.15. In some embodiments, the labyrinthin-derived peptide has a pI of less than about 3.4.

In some embodiments, the antigenic composition comprises a labyrinthin-derived peptide comprising a sequence selected from SEQ ID NO:2-32 (Table 2), or variant thereof. In some embodiments, the labyrinthin-derived peptide comprising a sequence selected from SEQ ID NO:2-32 (Table 2), or variant thereof, comprises one or two flanking amino acid sequences, the one or two flanking amino acid sequences added on the terminal ends of the core sequences provided in SEQ ID NO:2-32. In some embodiments, the labyrinthin-derived peptide comprising one or two flanking amino acid sequences is a peptide having a sequence similarity of at least about 60% similarity, such as at least about any of 65% similarity, 70% similarity, 75% similarity, 80% similarity, 85% similarity, 90% similarity, or 95% similarity, to a portion of labyrinthin (SEQ ID NO:1). In some embodiments, the flanking amino acid sequence is based on the sequence of a portion of labyrinthin (SEQ ID NO:1) and is a respective continuation of the labyrinthin sequence from each core sequence provided in SEQ ID NO:2-32, such as from one or two terminal ends of the core sequence. For example, for SEQ ID NO:3, a first flanking amino acid sequence of two amino acids to the left of SEQ ID NO:3 would be Pro-Ala, and a second flanking amino acid sequence of two amino acids to the right of SEQ ID NO:3 would be Glu-Ala.

TABLE 2

| Amino acid sequences of labyrinthin-derived peptides or portions thereof. | |
| --- | --- |
| | Amino acid sequence |
| SEQ ID NO: 2 | Glu-Pro-Ala |
| SEQ ID NO: 3 | Val-Pro-Pro-Glu |
| SEQ ID NO: 4 | Glu-Pro-His |
| SEQ ID NO: 5 | Glu-Pro-Glu |
| SEQ ID NO: 6 | Val-Pro-Val |
| SEQ ID NO: 7 | Glu-Pro-Gln |
| SEQ ID NO: 8 | Gly-Pro-Thr |
| SEQ ID NO: 9 | Asn-Pro-Asp |
| SEQ ID NO: 10 | Glu-Pro-Val |
| SEQ ID NO: 11 | Glu-Pro-Leu |
| SEQ ID NO: 12 | Ala-Pro-Pro-Glu |
| SEQ ID NO: 13 | Asn-Pro-Val |
| SEQ ID NO: 14 | Phe-Pro-Val |
| SEQ ID NO: 15 | Val-Pro-Pro-Asp |
| SEQ ID NO: 16 | Glu-Pro-Ala-Val-Pro-Pro-Glu |
| SEQ ID NO: 17 | Val-Pro-Pro-Glu-Glu-Ala-Glu-Pro-His |
| SEQ ID NO: 18 | Glu-Pro-His-Thr-Glu-Pro-Glu |
| SEQ ID NO: 19 | Glu-Pro-Glu-Glu-Gln-Val-Pro-Val |
| SEQ ID NO: 20 | Val-Pro-Val-Glu-Ala-Glu-Pro-Gln |
| SEQ ID NO: 21 | Gly-Pro-Thr-Gly-Glu-Pro-Gln |
| SEQ ID NO: 22 | Asn-Pro-Asp-Ser-Ser-Glu-Pro-Val |
| SEQ ID NO: 23 | Ala-Pro-Pro-Glu-Asp-Asn-Pro-Val |
| SEQ ID NO: 24 | Phe-Pro-Val-Glu-Glu-Gln-Gln-Glu-Val-Pro-Pro-Asp |
| SEQ ID NO: 25 | Asp-Gly-Pro-Thr-Gly-Glu-Pro-Gln-Gln-Glu |
| SEQ ID NO: 26 | Glu-Gln-Glu-Asn-Pro-Asp-Ser-Ser-Glu-Pro-Val |
| SEQ ID NO: 27 | Ala-Pro-Pro-Glu-Asp-Asn-Pro-Val-Glu-Asp |
| SEQ ID NO: 28 | Glu-Glu-Gln-Gln-Glu-Val-Pro-Pro-Asp |
| SEQ ID NO: 29 | Gly-Glu-Asp-Leu-Gln-Gln-Glu-Asp-Gly-Pro-Thr-Gly-Glu-Pro-Gln-Gln-Glu-Asp-Asp-Glu-Phe-Leu |
| SEQ ID NO: 30 | Asp-Met-Glu-Glu-Met-Met-Ser-Glu-Gln-Glu-Asn-Pro-Asp-Ser-Ser-Glu-Pro-Val-Val-Glu-Asp-Glu |
| SEQ ID NO: 31 | Asn-Glu-Gly-Ile-Glu-Ile-Thr-Glu-Val-Thr-Ala-Pro-Pro-Glu-Asp-Asn-Pro-Val-Glu-Asp-Ser-Gln |
| SEQ ID NO: 32 | Asp-Ser-Gln-Val-Ile-Val-Glu-Glu-Val-Ser-Ile-Phe-Pro-Val-Glu-Glu-Gln-Gln-Glu-Val-Pro-Pro-Asp |

In some embodiments, the antigenic composition comprises a labyrinthin-derived peptide comprising SEQ ID NO:2 or a variant thereof, wherein the labyrinthin-derived peptide comprises a T-cell epitope and/or a B-cell epitope. In some embodiments, the labyrinthin-derived peptide comprises SEQ ID NO:2 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:2 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:2 or a variant thereof, wherein 1 or or 2 amino acids of the sequence of SEQ ID NO:2 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:3 or a variant thereof, wherein the labyrinthin-derived peptide comprises a T-cell epitope and/or a B-cell epitope. In some embodiments, the labyrinthin-derived peptide comprises SEQ ID NO:3 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:3 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:3 or a variant thereof, wherein 1 or or 2 amino acids of the sequence of SEQ ID NO:3 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:4 or a variant thereof, wherein the labyrinthin-derived peptide comprises a T-cell epitope and/or a B-cell epitope. In some embodiments, the labyrinthin-derived peptide comprises SEQ ID NO:4 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:4 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:4 or a variant thereof, wherein 1 or 2 amino acids of the sequence of SEQ ID NO:4 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:5 or a variant thereof, wherein the labyrinthin-derived peptide comprises a T-cell epitope and/or a B-cell epitope. In some embodiments, the labyrinthin-derived peptide comprises SEQ ID NO:5 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:5 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:5 or a variant thereof, wherein 1 or 2 amino acids of the sequence of SEQ ID NO:5 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:7 or a variant thereof, wherein the labyrinthin-derived peptide comprises a T-cell epitope and/or a B-cell epitope. In some embodiments, the labyrinthin-derived peptide comprises SEQ ID NO:7 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:7 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:7 or a variant thereof, wherein 1 or 2 amino acids of the sequence of SEQ ID NO:7 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:8 or a variant thereof, wherein the labyrinthin-derived peptide comprises a T-cell epitope and/or a B-cell epitope. In some embodiments, the labyrinthin-derived peptide comprises SEQ ID NO:8 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:8 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:8 or a variant thereof, wherein 1 or 2 amino acids of the sequence of SEQ ID NO:8 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:9 or a variant thereof, wherein the labyrinthin-derived peptide comprises a T-cell epitope and/or a B-cell epitope. In some embodiments, the labyrinthin-derived peptide comprises SEQ ID NO:9 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:9 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:9 or a variant thereof, wherein 1 or 2 amino acids of the sequence of SEQ ID NO:9 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:10 or a variant thereof, wherein the labyrinthin-derived peptide comprises a T-cell epitope and/or a B-cell epitope. In some embodiments, the labyrinthin-derived peptide comprises SEQ ID NO:10 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:10 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:10 or a variant thereof, wherein 1 or 2 amino acids of the sequence of SEQ ID NO:10 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:11 or a variant thereof, wherein the labyrinthin-derived peptide comprises a T-cell epitope and/or a B-cell epitope. In some embodiments, the labyrinthin-derived peptide comprises SEQ ID NO:11 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:11 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:11 or a variant thereof, wherein 1 or 2 amino acids of the sequence of SEQ ID NO:11 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:12 or a variant thereof, wherein the labyrinthin-derived peptide comprises a T-cell epitope and/or a B-cell epitope. In some embodiments, the labyrinthin-derived peptide comprises SEQ ID NO:12 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:12 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity.

In some embodiments, the labyrinthin-derived peptide comprises SEQ ID NO:12 or a variant thereof, wherein 1 or 2 amino acids of the sequence of SEQ ID NO:12 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:13 or a variant thereof, wherein the labyrinthin-derived peptide comprises a T-cell epitope and/or a B-cell epitope. In some embodiments, the labyrinthin-derived peptide comprises SEQ ID NO:13 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:13 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:13 or a variant thereof, wherein 1 or 2 amino acids of the sequence of SEQ ID NO:13 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:14 or a variant thereof, wherein the labyrinthin-derived peptide comprises a T-cell epitope and/or a B-cell epitope. In some embodiments, the labyrinthin-derived peptide comprises SEQ ID NO:14 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:14 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:14 or a variant thereof, wherein 1 or 2 amino acids of the sequence of SEQ ID NO:14 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:15 or a variant thereof, wherein the labyrinthin-derived peptide comprises a T-cell epitope and/or a B-cell epitope. In some embodiments, the labyrinthin-derived peptide comprises SEQ ID NO:15 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:15 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:15 or a variant thereof, wherein 1 or 2 amino acids of the sequence of SEQ ID NO:15 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:16 or a variant thereof, wherein the labyrinthin-derived peptide comprises a T-cell epitope and/or a B-cell epitope. In some embodiments, the labyrinthin-derived peptide comprises SEQ ID NO:16 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:16 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:16 or a variant thereof, wherein 1, 2, or 3 amino acids of the sequence of SEQ ID NO:16 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:17 or a variant thereof, wherein the labyrinthin-derived peptide comprises a T-cell epitope and/or a B-cell epitope. In some embodiments, the labyrinthin-derived peptide comprises SEQ ID NO:17 or a variant thereof, wherein the labyrinthin-derived peptide is between 9 and 50 amino acids in length, such as between any of 9 and 25 amino acids in length, 9 to 13 amino acids in length, or 21 and 25 amino acids in length. In some embodiments, the labyrinthin-derived peptide comprises SEQ ID NO:17 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:17 or a variant thereof, wherein 1, 2, or 3 amino acids of the sequence of SEQ ID NO:17 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:18 or a variant thereof, wherein the labyrinthin-derived peptide comprises a T-cell epitope and/or a B-cell epitope. In some embodiments, the labyrinthin-derived peptide comprises SEQ ID NO:18 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:18 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:18 or a variant thereof, wherein 1, 2, or 3 amino acids of the sequence of SEQ ID NO:18 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:19 or a variant thereof, wherein the labyrinthin-derived peptide comprises a T-cell epitope and/or a B-cell epitope. In some embodiments, the labyrinthin-derived peptide comprises SEQ ID NO:19 or a variant thereof, wherein the labyrinthin-derived peptide is between 8 and 50 amino acids in length, such as between any of 10 and 25 amino acids in length, 8 to 13 amino acids in length, or 21 and 25 amino acids in length. In some embodiments, the labyrinthin-derived peptide comprises SEQ ID NO:19 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:19 or a variant thereof, wherein 1, 2, or 3 amino acids of the sequence of SEQ ID NO:19 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:20 or a variant thereof, wherein the labyrinthin-derived peptide comprises a T-cell epitope and/or a B-cell epitope. In some embodiments, the labyrinthin-derived peptide comprises SEQ ID NO:20 or a variant thereof, wherein the labyrinthin-derived peptide is between 8 and 50 amino acids in length, such as between any of 10 and 25 amino acids in length, 8 to 13 amino acids in length, or 21 and 25 amino acids in length. In some embodiments, the labyrinthin-derived peptide comprises SEQ ID NO:20 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:20 or a variant thereof, wherein 1, 2, or 3 amino acids of the sequence of SEQ ID NO:20 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:21 or a variant thereof, wherein the labyrinthin-derived peptide comprises a T-cell epitope and/or a B-cell epitope. In some embodiments, the labyrinthin-derived peptide comprises SEQ ID NO:21 or a variant thereof, wherein the labyrinthin-derived peptide is between 7 and 50 amino acids in length, such as between any of 7 and 25 amino acids in length, 7 to 13 amino acids in length, or 21 and 25 amino acids in length. In some embodiments, the labyrinthin-derived peptide comprises SEQ ID NO:21 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:21 or a variant thereof, wherein 1, 2, or 3 amino acids of the sequence of SEQ ID NO:21 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:22 or a variant thereof, wherein the labyrinthin-derived peptide comprises a T-cell epitope and/or a B-cell epitope. In some embodiments, the labyrinthin-derived peptide comprises SEQ ID NO:22 or a variant thereof, wherein the labyrinthin-derived peptide is between 8 and 50 amino acids in length, such as between any of 10 and 25 amino acids in length, 8 to 13 amino acids in length, or 21 and 25 amino acids in length. In some embodiments, the labyrinthin-derived peptide comprises SEQ ID NO:22 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:22 or a variant thereof, wherein 1, 2, or 3 amino acids of the sequence of SEQ ID NO:22 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:23 or a variant thereof, wherein the labyrinthin-derived peptide comprises a T-cell epitope and/or a B-cell epitope. In some embodiments, the labyrinthin-derived peptide comprises SEQ ID NO:23 or a variant thereof, wherein the labyrinthin-derived peptide is between 8 and 50 amino acids in length, such as between any of 10 and 25 amino acids in length, 8 to 13 amino acids in length, or 21 and 25 amino acids in length. In some embodiments, the labyrinthin-derived peptide comprises SEQ ID NO:23 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:23 or a variant thereof, wherein 1, 2, or 3 amino acids of the sequence of SEQ ID NO:23 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:24 or a variant thereof, wherein the labyrinthin-derived peptide comprises a T-cell epitope and/or a B-cell epitope. In some embodiments, the labyrinthin-derived peptide comprises SEQ ID NO:24 or a variant thereof, wherein the labyrinthin-derived peptide is between 12 and 50 amino acids in length, such as between any of 12 and 25 amino acids in length, 12 to 13 amino acids in length, or 21 and 25 amino acids in length. In some embodiments, the labyrinthin-derived peptide comprises SEQ ID NO:24 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:24 or a variant thereof, wherein 1, 2, or 3 amino acids of the sequence of SEQ ID NO:24 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:25 or a variant thereof, wherein the labyrinthin-derived peptide comprises a T-cell epitope and a B-cell epitope. In some embodiments, the labyrinthin-derived peptide comprises SEQ ID NO:25 or a variant thereof, wherein the labyrinthin-derived peptide is between 11 and 50 amino acids in length, such as between any of 11 and 25 amino acids in length, 12 to 13 amino acids in length, or 21 and 25 amino acids in length. In some embodiments, the labyrinthin-derived peptide comprises SEQ ID NO:25 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:25 or a variant thereof, wherein 1, 2, or 3 amino acids of the sequence of SEQ ID NO:25 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:26 or a variant thereof, wherein the labyrinthin-derived peptide comprises a T-cell epitope and a B-cell epitope. In some embodiments, the labyrinthin-derived peptide comprises SEQ ID NO:26 or a variant thereof, wherein the labyrinthin-derived peptide is between 11 and 50 amino acids in length, such as between any of 11 and 25 amino acids in length, 12 to 13 amino acids in length, or 21 and 25 amino acids in length. In some embodiments, the labyrinthin-derived peptide comprises SEQ ID NO:26 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:26 or a variant thereof, wherein 1, 2, or 3 amino acids of the sequence of SEQ ID NO:26 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:27 or a variant thereof, wherein the labyrinthin-derived peptide comprises a T-cell epitope and a B-cell epitope. In some embodiments, the labyrinthin-derived peptide comprises SEQ ID NO:27 or a variant thereof, wherein the labyrinthin-derived peptide is between 11 and 50 amino acids in length, such as between any of 11 and 25 amino acids in length, 11 to 13 amino acids in length, or 21 and 25 amino acids in length. In some embodiments, the labyrinthin-derived peptide comprises SEQ ID NO:27 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:27 or a variant thereof, wherein 1, 2, or 3 amino acids of the sequence of SEQ ID NO:27 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:28 or a variant thereof, wherein the labyrinthin-derived peptide comprises a T-cell epitope and/or a B-cell epitope. In some embodiments, the labyrinthin-derived peptide comprises SEQ ID NO:28 or a variant thereof, wherein the labyrinthin-derived peptide is between 10 and 50 amino acids in length, such as between any of 10 and 25 amino acids in length, 10 to 13 amino acids in length, or 21 and 25 amino acids in length. In some embodiments, the labyrinthin-derived peptide comprises SEQ ID NO:28 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:28 or a variant thereof, wherein 1, 2, or 3 amino acids of the sequence of SEQ ID NO:28 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:29 or a variant thereof, wherein the labyrinthin-derived peptide comprises a T-cell epitope and a B-cell epitope. In some embodiments, the labyrinthin-derived peptide comprises SEQ ID NO:29 or a variant thereof, wherein the labyrinthin-derived peptide is between 22 and 50 amino acids in length. In some embodiments, the labyrinthin-derived peptide comprises SEQ ID NO:29 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:29 or a variant thereof, wherein 1, 2, 3, 4, or 5 amino acids of the sequence of SEQ ID NO:29 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:30 or a variant thereof, wherein the labyrinthin-derived peptide comprises a T-cell epitope and a B-cell epitope. In some embodiments, the labyrinthin-derived peptide comprises SEQ ID NO:30 or a variant thereof, wherein the labyrinthin-derived peptide is between 22 and 50 amino acids in length. In some embodiments, the labyrinthin-derived peptide comprises SEQ ID NO:30 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:30 or a variant thereof, wherein 1, 2, 3, 4, or 5 amino acids of the sequence of SEQ ID NO:30 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:31 or a variant thereof, wherein the labyrinthin-derived peptide comprises a T-cell epitope and a B-cell epitope. In some embodiments, the labyrinthin-derived peptide comprises SEQ ID NO:31 or a variant thereof, wherein the labyrinthin-derived peptide is between 22 and 50 amino acids in length. In some embodiments, the labyrinthin-derived peptide comprises SEQ ID NO:31 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:31 or a variant thereof, wherein 1, 2, 3, 4, or 5 amino acids of the sequence of SEQ ID NO:31 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises a labyrinthin-derived peptide comprising SEQ ID NO:32 or a variant thereof, wherein the labyrinthin-derived peptide comprises a T-cell epitope and a B-cell epitope. In some embodiments, the labyrinthin-derived peptide comprises SEQ ID NO:32 or a variant thereof, wherein the labyrinthin-derived peptide is between 23 and 50 amino acids in length. In some embodiments, the labyrinthin-derived peptide comprises SEQ ID NO:32 or a variant thereof, wherein the labyrinthin-derived peptide has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the labyrinthin-derived peptide comprises SEQ ID NO:32 or a variant thereof, wherein 1, 2, 3, 4, or 5 amino acids of the sequence of SEQ ID NO:32 are deleted, substituted, inserted, and/or added to the labyrinthin-derived peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the antigenic composition comprises one or more labyrinthin-derived peptides selected from the group comprising: (a) a first peptide comprising SEQ ID NO:25 or a variant thereof; (b) a second peptide comprising SEQ ID NO:26 or a variant thereof; (c) a third peptide comprising SEQ ID NO:27 or a variant thereof; and (d) a fourth peptide comprising SEQ ID NO:28 or a variant thereof, wherein each peptide comprises a T-cell epitope and a B-cell epitope.

In some embodiments, the first peptide comprising SEQ ID NO:25 or a variant thereof is between 11 and 50 amino acids in length, such as between any one of 11 and 45 amino acids in length, 11 and 40 amino acids in length, 11 and 35 amino acids in length, 11 and 30 amino acids in length, 11 and 25 amino acids in length, 15 and 30 amino acids in length, 20 and 30 amino acids in length, or 21 and 25 amino acids in length. In some embodiments, the first peptide comprising SEQ ID NO:25 or a variant thereof is at least 11 amino acids in length, such as least any of 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length. In some embodiments, the first peptide comprising SEQ ID NO:25 or a variant thereof is no greater than 50 amino acids in length, such as no greater than any of 49 amino acids in length, 48 amino acids in length, 47 amino acids in length, 46 amino acids in length, 45 amino acids in length, 44 amino acids in length, 43 amino acids in length, 42 amino acids in length, 41 amino acids in length, 40 amino acids in length, 39 amino acids in length, 38 amino acids in length, 37 amino acids in length, 36 amino acids in length, 35 amino acids in length, 34 amino acids in length, 33 amino acids in length, 32 amino acids in length, 31 amino acids in length, 30 amino acids in length, 29 amino acids in length, 28 amino acids in length, 27 amino acids in length, 26 amino acids in length, 25 amino acids in length, 24 amino acids in length, 23 amino acids in length, 22 amino acids in length, 21 amino acids in length, 20 amino acids in length, 19 amino acids in length, 18 amino acids in length, 17 amino acids in length, 16 amino acids in length, or 15 amino acids in length. In some embodiments, the first peptide comprising SEQ ID NO:25 or a variant thereof is 11 amino acids in length, 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length.

In some embodiments, the first peptide comprises SEQ ID NO:25. In some embodiments, the first peptide comprising SEQ ID NO:25 is SEQ ID NO:29. In some embodiments, the first peptide comprising SEQ ID NO:25 or variant thereof is a variant of SEQ ID NO:29, wherein at least one amino acid of the sequence of SEQ ID NO:29 is substituted, deleted, inserted, and/or added to the first peptide. In some embodiments, the first peptide comprising SEQ ID NO:25 or variant thereof is a variant of SEQ ID NO:29, wherein 1, 2, 3, 4, or 5 amino acids of the sequence of SEQ ID NO:29 are deleted, substituted, inserted, and/or added to the first peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the first peptide comprising SEQ ID NO:25 or a variant thereof is substantially homologous to a portion of labyrinthin (SEQ ID NO:1). In some embodiments, the first peptide comprising SEQ ID NO:25 or a variant thereof has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the variant of SEQ ID NO:29 has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity.

In some embodiments, the second peptide comprising SEQ ID NO:26 or a variant thereof is between 12 and 50 amino acids in length, such as between any one of 12 and 45 amino acids in length, 12 and 40 amino acids in length, 12 and 35 amino acids in length, 12 and 30 amino acids in length, 12 and 25 amino acids in length, 15 and 30 amino acids in length, 20 and 30 amino acids in length, or 21 and 25 amino acids in length. In some embodiments, the second peptide comprising SEQ ID NO:26 or a variant thereof is at least 12 amino acids in length, such as least any of 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length. In some embodiments, the second peptide comprising SEQ ID NO:26 or a variant thereof is no greater than 50 amino acids in length, such as no greater than any of 49 amino acids in length, 48 amino acids in length, 47 amino acids in length, 46 amino acids in length, 45 amino acids in length, 44 amino acids in length, 43 amino acids in length, 42 amino acids in length, 41 amino acids in length, 40 amino acids in length, 39 amino acids in length, 38 amino acids in length, 37 amino acids in length, 36 amino acids in length, 35 amino acids in length, 34 amino acids in length, 33 amino acids in length, 32 amino acids in length, 31 amino acids in length, 30 amino acids in length, 29 amino acids in length, 28 amino acids in length, 27 amino acids in length, 26 amino acids in length, 25 amino acids in length, 24 amino acids in length, 23 amino acids in length, 22 amino acids in length, 21 amino acids in length, 20 amino acids in length, 19 amino acids in length, 18 amino acids in length, 17 amino acids in length, 16 amino acids in length, or 15 amino acids in length. In some embodiments, the second peptide comprising SEQ ID NO:26 or a variant thereof is 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length.

In some embodiments, the second peptide comprises SEQ ID NO:26. In some embodiments, the second peptide comprising SEQ ID NO:26 is SEQ ID NO:30. In some embodiments, the second peptide comprising SEQ ID NO:26 or variant thereof is a variant of SEQ ID NO:30, wherein at least one amino acid of the sequence of SEQ ID NO:26 is substituted, deleted, inserted, and/or added to the first peptide. In some embodiments, the second peptide comprising SEQ ID NO:26 or variant thereof is a variant of SEQ ID NO:30, wherein 1, 2, 3, 4, or 5 amino acids of the sequence of SEQ ID NO:30 are deleted, substituted, inserted, and/or added to the first peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the second peptide comprising SEQ ID NO:26 or a variant thereof is substantially homologous to a portion of labyrinthin (SEQ ID NO:1). In some embodiments, the second peptide comprising SEQ ID NO:26 or a variant thereof has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the variant of SEQ ID NO:30 has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity.

In some embodiments, the third peptide comprising SEQ ID NO:27 or variant thereof is between 11 and 50 amino acids in length, such as between any one of 11 and 45 amino acids in length, 11 and 40 amino acids in length, 11 and 35 amino acids in length, 11 and 30 amino acids in length, 11 and 25 amino acids in length, 15 and 30 amino acids in length, 20 and 30 amino acids in length, or 21 and 25 amino acids in length. In some embodiments, the third peptide comprising SEQ ID NO:27 or a variant thereof is at least 11 amino acids in length, such as least any of 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length. In some embodiments, the third peptide comprising SEQ ID NO:27 or a variant thereof is no greater than 50 amino acids in length, such as no greater than any of 49 amino acids in length, 48 amino acids in length, 47 amino acids in length, 46 amino acids in length, 45 amino acids in length, 44 amino acids in length, 43 amino acids in length, 42 amino acids in length, 41 amino acids in length, 40 amino acids in length, 39 amino acids in length, 38 amino acids in length, 37 amino acids in length, 36 amino acids in length, 35 amino acids in length, 34 amino acids in length, 33 amino acids in length, 32 amino acids in length, 31 amino acids in length, 30 amino acids in length, 29 amino acids in length, 28 amino acids in length, 27 amino acids in length, 26 amino acids in length, 25 amino acids in length, 24 amino acids in length, 23 amino acids in length, 22 amino acids in length, 21 amino acids in length, 20 amino acids in length, 19 amino acids in length, 18 amino acids in length, 17 amino acids in length, 16 amino acids in length, or 15 amino acids in length. In some embodiments, the third peptide comprising SEQ ID NO:27 or a variant thereof is 11 amino acids in length, 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length.

In some embodiments, the third peptide comprises SEQ ID NO:27. In some embodiments, the third peptide comprising SEQ ID NO:27 is SEQ ID NO:31. In some embodiments, the third peptide comprising SEQ ID NO:27 or variant thereof is a variant of SEQ ID NO:31, wherein at least one amino acid of the sequence of SEQ ID NO:27 is substituted, deleted, inserted, and/or added to the first peptide. In some embodiments, the third peptide comprising SEQ ID NO:27 or variant thereof is a variant of SEQ ID NO:31, wherein 1, 2, 3, 4, or 5 amino acids of the sequence of SEQ ID NO:31 are deleted, substituted, inserted, and/or added to the first peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the third peptide comprising SEQ ID NO:27 or a variant thereof is substantially homologous to a portion of labyrinthin (SEQ ID NO:1). In some embodiments, the third peptide comprising SEQ ID NO:27 or a variant thereof has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the variant of SEQ ID NO:31 has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity.

In some embodiments, the fourth peptide comprising SEQ ID NO:28 or a variant thereof is between 10 and 50 amino acids in length, such as between any one of 10 and 45 amino acids in length, 10 and 40 amino acids in length, 10 and 35 amino acids in length, 10 and 30 amino acids in length, 10 and 25 amino acids in length, 10 and 30 amino acids in length, 20 and 30 amino acids in length, or 21 and 25 amino acids in length. In some embodiments, the fourth peptide comprising SEQ ID NO:28 or a variant thereof is at least 10 amino acids in length, such as least any of 11 amino acids in length, 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length. In some embodiments, the fourth peptide comprising SEQ ID NO:28 or a variant thereof is no greater than 50 amino acids in length, such as no greater than any of 49 amino acids in length, 48 amino acids in length, 47 amino acids in length, 46 amino acids in length, 45 amino acids in length, 44 amino acids in length, 43 amino acids in length, 42 amino acids in length, 41 amino acids in length, 40 amino acids in length, 39 amino acids in length, 38 amino acids in length, 37 amino acids in length, 36 amino acids in length, 35 amino acids in length, 34 amino acids in length, 33 amino acids in length, 32 amino acids in length, 31 amino acids in length, 30 amino acids in length, 29 amino acids in length, 28 amino acids in length, 27 amino acids in length, 26 amino acids in length, 25 amino acids in length, 24 amino acids in length, 23 amino acids in length, 22 amino acids in length, 21 amino acids in length, 20 amino acids in length, 19 amino acids in length, 18 amino acids in length, 17 amino acids in length, 16 amino acids in length, or 15 amino acids in length. In some embodiments, the fourth peptide comprising SEQ ID NO:28 or a variant thereof is 10 amino acids in length, 11 amino acids in length, 12 amino acids in length, 13 amino acids in length, 14 amino acids in length, 15 amino acids in length, 16 amino acids in length, 17 amino acids in length, 18 amino acids in length, 19 amino acids in length, 20 amino acids in length, 21 amino acids in length, 22 amino acids in length, 23 amino acids in length, 24 amino acids in length, 25 amino acids in length, 26 amino acids in length, 27 amino acids in length, 28 amino acids in length, 29 amino acids in length, 30 amino acids in length, 31 amino acids in length, 32 amino acids in length, 33 amino acids in length, 34 amino acids in length, 35 amino acids in length, 36 amino acids in length, 37 amino acids in length, 38 amino acids in length, 39 amino acids in length, 40 amino acids in length, 41 amino acids in length, 42 amino acids in length, 43 amino acids in length, 44 amino acids in length, 45 amino acids in length, 46 amino acids in length, 47 amino acids in length, 48 amino acids in length, 49 amino acids in length, or 50 amino acids in length.

In some embodiments, the fourth peptide comprises SEQ ID NO:28. In some embodiments, the fourth peptide comprising SEQ ID NO:28 is SEQ ID NO:32. In some embodiments, the fourth peptide comprising SEQ ID NO:28 or variant thereof is a variant of SEQ ID NO:32, wherein at least one amino acid of the sequence of SEQ ID NO:32 is substituted, deleted, inserted, and/or added to the first peptide. In some embodiments, the fourth peptide comprising SEQ ID NO:28 or variant thereof is a variant of SEQ ID NO:32, wherein 1, 2, 3, 4, or 5 amino acids of the sequence of SEQ ID NO:32 are deleted, substituted, inserted, and/or added to the first peptide, and wherein when a substitution, insertion, and/or addition is present, a moiety is substituted, inserted, and/or added to the sequence. In some embodiments, the moiety that is substituted, inserted, or added is a natural amino acid (e.g., α-amino acid or a L-amino acid or a D-amino acid) or a non-natural amino acid. In some embodiments, the moiety that is substituted, inserted, or added is an amino acid substitute or a linker.

In some embodiments, the fourth peptide comprising SEQ ID NO:28 or a variant thereof is substantially homologous to a portion of labyrinthin (SEQ ID NO:1). In some embodiments, the fourth peptide comprising SEQ ID NO:28 or a variant thereof has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity. In some embodiments, the variant of SEQ ID NO:32 has a sequence similarity of at least about 60% similarity to a portion of labyrinthin (SEQ ID NO:1), such as at least about any of 65% similarity, 70% similarity, 75% similarity, 80% similarity, 85% similarity, 90% similarity, or 95% similarity.

In some embodiments, for any of the antigenic compositions disclosed herein, the one or more of the labyrinthin-derived peptides are soluble in a solution. In some embodiments, the one or more of the labyrinthin-derived peptides have a solubility in a solution of at least about 0.1 mg/mL, such as at least about any of 0.5 mg/mL, 1 mg/ml, 2 mg/ml, 3 mg/ml, 4 mg/ml, 5 mg/ml, 6 mg/ml, 7 mg/ml, 8 mg/ml, 9 mg/ml, or 10 mg/ml. In some embodiments, the solution is a pharmaceutically acceptable vehicle. In some embodiments, the solution comprises one or more of water, a buffer, such as PBS, and a salt solution, such as a sodium chloride solution.

In some embodiments, for any of the antigenic compositions disclosed herein, each of the one or more of the labyrinthin-derived peptides have a purity of at least about 90%, such as at least about any of 91%, 92%, 93%, 94%, 95%, 96%, 97%, 98%, or 99%. Methods for determining peptide purity are known in the art, such as using a high-performance liquid chromatography technique.

In some embodiments, for any of the antigenic compositions disclosed herein, one or more of the labyrinthin-derived peptides therein activates both T-cell and/or B-cell adaptive immune responses. In some embodiments, for any of the antigenic compositions disclosed herein, each labyrinthin-derived peptide activates T-cell and B-cell adaptive immune responses. In some embodiments, activation of the T-cell adaptive immune response results in production of target-specific receptors, e.g., an anti-labyrinthin-derived peptide epitope T-cell receptor. In some embodiments, activation of the T-cell adaptive immune response is via class I major histocompatibility complexes (MHC I). In some embodiments, activation of the T-cell adaptive immune response is via class II major histocompatibility complexes (MHC II). In some embodiments, activation of the T-cell adaptive immune response is via MHC I and MHC II. In some embodiments, activation of the B-cell adaptive immune response results in production of target-specific immunoglobulins, e.g., an anti-labyrinthin-derived peptide epitope antibody. Methods for assessing labyrinthin-derived peptide activation of T-cell and B-cell adaptive immune responses, and if a peptide is a T-cell and/or B-cell epitope, are known in the art. See, e.g., Bercovici, N. et al., *Clin*

*Diagn Lab Immunol,* 2000, 7, 859-864; and McAllister, E. J. et al., *J Immunol,* 2017, 199, 2998-3003.

In some embodiments, for any of the antigenic compositions disclosed herein, at least one of the one or more labyrinthin-derived peptides of the antigenic composition is conjugated. In some embodiments, the labyrinthin-derived peptide is conjugated to a carrier molecule. In some embodiments, the labyrinthin-derived peptide is conjugated to a protein, such as ovalbumin, albumin, keyhole limpet haemocyanin (KLH), diphtheria toxoid, tetanus toxoid, or CRM197. In some embodiments, the labyrinthin-derived peptide is conjugated to a lipid. In some embodiments, the labyrinthin-derived peptide is conjugated to an adjuvant. In some embodiments, the labyrinthin-derived peptide is conjugated to an immuno-effective (such as an immune enhancing) adjuvant. In some embodiments, the labyrinthin-derived peptide is conjugated to one or more other labyrinthin-derived peptides. In some embodiments, the labyrinthin-derived peptide is conjugated to one or more other labyrinthin-derived peptides, wherein the resulting sequence of the peptide is not a sequence of labyrinthin or a portion thereof (SEQ ID NO:1). For example, in some embodiments, the first labyrinthin-derived peptide is conjugated to a second labyrinthin-derived peptide, wherein the resulting sequence of the first peptide and the second peptide is not a sequence of labyrinthin or a portion thereof (SEQ ID NO:1). In some embodiments, the labyrinthin-derived peptide is conjugated via a linker, such as a cross-linker. In some embodiments, the labyrinthin-derived peptide is conjugated to a linker.

In some embodiments, the antigenic composition comprises one or more labyrinthin-derived peptides selected from the group comprising: (a) a first peptide comprising SEQ ID NO:25 or a variant thereof, (b) a second peptide comprising SEQ ID NO:26 or a variant thereof; (c) a third peptide comprising SEQ ID NO:27 or a variant thereof, and (d) a fourth peptide comprising SEQ ID NO:28 or a variant thereof, wherein each peptide comprises a T-cell epitope and a B-cell epitope. For example, in some embodiments, the antigenic composition comprises a first peptide comprising SEQ ID NO:25 or a variant thereof, wherein the first peptide comprises a T-cell epitope and a B-cell epitope. In some embodiments, the one or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the antigenic composition comprises a first peptide comprising SEQ ID NO:29 or a variant thereof, wherein the first peptide comprises a T-cell epitope and a B-cell epitope. In some embodiments, the antigenic composition comprises a first peptide, wherein the first peptide is SEQ ID NO:29, and wherein the first peptide comprises a T-cell epitope and a B-cell epitope. In some embodiments, each peptide of the antigenic composition activates T-cell and B-cell adaptive immune responses.

In some embodiments, the antigenic composition comprises one or more labyrinthin-derived peptides selected from the group comprising: (a) a first peptide comprising SEQ ID NO:25 or a variant thereof, (b) a second peptide comprising SEQ ID NO:26 or a variant thereof, (c) a third peptide comprising SEQ ID NO:27 or a variant thereof, and (d) a fourth peptide comprising SEQ ID NO:28 or a variant thereof. In some embodiments, the antigenic composition comprises: (a) a first peptide comprising SEQ ID NO:25 or a variant thereof, (b) a second peptide comprising SEQ ID NO:26 or a variant thereof; (c) a third peptide comprising SEQ ID NO:27 or a variant thereof; and (d) a fourth peptide comprising SEQ ID NO:28 or a variant thereof. In some embodiments, the antigenic composition comprises: (a) a first peptide comprising SEQ ID NO:25 or a variant thereof, (b) a second peptide comprising SEQ ID NO:26 or a variant thereof; (c) a third peptide comprising SEQ ID NO:27 or a variant thereof, and (d) a fourth peptide comprising SEQ ID NO:28 or a variant thereof, wherein these are the only four labyrinthin-derived peptides in the antigenic composition. In some embodiments, the labyrinthin-derived peptides are between 21 and 24 amino acids in length, such as 22 or 23 amino acids in length. In some embodiments, the antigen composition comprising a peptide comprising SEQ ID NO:25 or a variant thereof comprises SEQ ID NO:29 or a variant thereof. In some embodiments, the antigen composition comprising a peptide comprising SEQ ID NO:26 or a variant thereof comprises SEQ ID NO:30 or a variant thereof. In some embodiments, the antigen composition comprising a peptide comprising SEQ ID NO:27 or a variant thereof comprises SEQ ID NO:31 or a variant thereof. In some embodiments, the antigen composition comprising a peptide comprising SEQ ID NO:28 or a variant thereof comprises SEQ ID NO:32 or a variant thereof. In some embodiments, the antigenic composition comprises: (a) a first peptide comprising SEQ ID NO:29 or a variant thereof, (b) a second peptide comprising SEQ ID NO:30 or a variant thereof; (c) a third peptide comprising SEQ ID NO:31 or a variant thereof, and (d) a fourth peptide comprising SEQ ID NO:32 or a variant thereof, wherein these are the only four labyrinthin-derived peptides in the antigenic composition. In some embodiments, the labyrinthin-derived peptide comprises a T-cell epitope and/or a B-cell epitope.

In some embodiments, the antigenic composition comprises a second peptide comprising SEQ ID NO:26 or a variant thereof, wherein the second peptide comprises a T-cell epitope and a B-cell epitope. In some embodiments, the one or more labyrinthin-derived peptides are between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the antigenic composition comprises a second peptide comprising SEQ ID NO:30 or a variant thereof, wherein the second peptide comprises a T-cell epitope and a B-cell epitope. In some embodiments, the antigenic composition comprises a second peptide, wherein the second peptide is SEQ ID NO:30, and wherein the second peptide comprises a T-cell epitope and a B-cell epitope. In some embodiments, each peptide of the antigenic composition activates T-cell and B-cell adaptive immune responses.

In some embodiments, the antigenic composition comprises a third peptide comprising SEQ ID NO:27 or a variant thereof, wherein the third peptide comprises a T-cell epitope and a B-cell epitope. In some embodiments, the one or more labyrinthin-derived peptides are between 21 and 24 amino acids in length, such as 22 or 23 amino acids in length. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises a third peptide comprising SEQ ID NO:31 or a variant thereof, wherein the third peptide comprises a T-cell epitope and a B-cell epitope. In some embodiments, the antigenic composition comprises a third peptide, wherein the third peptide is SEQ ID NO:31, and wherein the third peptide comprises a T-cell epitope and a B-cell epitope.

In some embodiments, the antigenic composition comprises a fourth peptide comprising SEQ ID NO:28 or a variant thereof, wherein the fourth peptide comprises a T-cell epitope and a B-cell epitope. In some embodiments, the one or more labyrinthin-derived peptides are between 21 and 24 amino acids in length, such as 22 or 23 amino acids in length. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises a fourth peptide comprising SEQ ID NO:32 or a variant thereof, wherein the fourth peptide comprises a T-cell epitope and a B-cell epitope. In some embodiments, the antigenic composition comprises a fourth peptide, wherein the fourth peptide is SEQ ID NO:32, and wherein the fourth peptide comprises a T-cell epitope and a B-cell epitope. In some embodiments, each peptide of the antigenic composition activates T-cell and B-cell adaptive immune responses.

In some embodiments, the antigenic composition comprises two or more labyrinthin-derived peptides. For example, in some embodiments, the antigenic composition comprises: (a) a first peptide comprising SEQ ID NO:25 or a variant thereof; and (b) a second peptide comprising SEQ ID NO:26 or a variant thereof, wherein each peptide comprises a T-cell epitope and a B-cell epitope. In some embodiments, each of the two or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the antigenic composition comprises: (a) a first peptide comprising SEQ ID NO:29 or a variant thereof and (b) a second peptide comprising SEQ ID NO:30 or a variant thereof, wherein each peptide comprises a T-cell epitope and a B-cell epitope. In some embodiments, the antigenic composition comprises: (a) a first peptide, wherein the first peptide is SEQ ID NO:29; and (b) a second peptide, wherein the second peptide is SEQ ID NO:30, wherein each peptide comprises a T-cell epitope and a B-cell epitope. In some embodiments, each peptide of the antigenic composition activates T-cell and B-cell adaptive immune responses.

In some embodiments, the antigenic composition comprises: (a) a first peptide comprising SEQ ID NO:25 or a variant thereof and (b) a third peptide comprising SEQ ID NO:27 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises: (a) a first peptide comprising SEQ ID NO:29 or a variant thereof and (b) a third peptide comprising SEQ ID NO:31 or a variant thereof, wherein each peptide comprises a T-cell epitope and a B-cell epitope. In some embodiments, the antigenic composition comprises: (a) a first peptide, wherein the first peptide is SEQ ID NO:29; and (b) a third peptide, wherein the third peptide is SEQ ID NO:31, wherein each peptide comprises a T-cell epitope and a B-cell epitope.

In some embodiments, the antigenic composition comprises: (a) a first peptide comprising SEQ ID NO:25 or a variant thereof and (b) a fourth peptide comprising SEQ ID NO:28 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof and (b) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; and (b) a fourth peptide, wherein the fourth peptide is SEQ ID NO:32, wherein each peptide comprises a T-cell epitope and a B-cell epitope.

In some embodiments, the antigenic composition comprises: (a) a second peptide comprising SEQ ID NO:26 or a variant thereof and (b) a third peptide comprising SEQ ID NO:27 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises: (a) a second peptide comprising SEQ ID NO:30 or a variant thereof; and (b) a third peptide comprising SEQ ID NO:31 or a variant thereof, wherein each peptide comprises a T-cell epitope and a B-cell epitope. In some embodiments, the antigenic composition comprises: (a) a second peptide, wherein the second peptide is SEQ ID NO:30; and (b) a third peptide, wherein the third peptide is SEQ ID NO:31, wherein each peptide comprises a T-cell epitope and a B-cell epitope.

In some embodiments, the antigenic composition comprises: (a) a second peptide comprising SEQ ID NO:25 or a variant thereof, and (b) a fourth peptide comprising SEQ ID NO:28 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a second peptide comprising SEQ ID NO:30 or a variant thereof; and (b) a fourth peptide comprising SEQ ID NO:32 or a variant thereof, wherein each peptide comprises a T-cell epitope and a B-cell epitope. In some embodiments, the antigenic composition comprises: (a) a second peptide, wherein the second peptide is SEQ ID NO:30; and (b) a fourth peptide, wherein the fourth peptide is SEQ ID NO:32, wherein each peptide comprises a T-cell epitope and a B-cell epitope.

In some embodiments, the antigenic composition comprises: (a) a third peptide comprising SEQ ID NO:27 or a variant thereof, and (b) a fourth peptide comprising SEQ ID NO:28 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a third peptide comprising SEQ ID NO:31 or a variant thereof, and (b) a fourth peptide comprising SEQ ID NO:32 or a variant thereof, wherein each peptide comprises a T-cell epitope and a B-cell epitope. In some embodiments, the antigenic composition comprises: (a) a third peptide, wherein the third peptide is SEQ ID NO:31; and (b) a fourth peptide, wherein the fourth peptide is SEQ ID NO:32, wherein each peptide comprises a T-cell epitope and a B-cell epitope.

In some embodiments, the antigenic composition comprises three or more labyrinthin-derived peptides. For example, in some embodiments, the antigenic composition comprises: (a) a first peptide comprising SEQ ID NO:25 or a variant thereof; (b) a second peptide comprising SEQ ID NO:26 or a variant thereof, and (c) a third peptide comprising SEQ ID NO:27 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises: (a) a first peptide comprising SEQ ID NO:29 or a variant thereof, (b) a second peptide comprising SEQ ID NO:30 or a variant thereof, and (c) a third peptide comprising SEQ ID NO:31 or a variant thereof, wherein each peptide comprises a T-cell epitope and a B-cell epitope. In some embodiments, the antigenic composition comprises: (a) a first peptide, wherein the first peptide is SEQ ID NO:29; (b) a second peptide, wherein the second peptide is SEQ ID NO:30; and (c) a third peptide, wherein the third peptide is SEQ ID NO:31, wherein each peptide comprises a T-cell epitope and a B-cell epitope.

In some embodiments, the antigenic composition comprises: (a) a first peptide comprising SEQ ID NO:25 or a variant thereof; (b) a second peptide comprising SEQ ID NO:26 or a variant thereof; and (c) a fourth peptide comprising SEQ ID NO:28 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof (b) a second peptide comprising SEQ ID NO:30 or a variant thereof and (c) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; (b) a second peptide, wherein the second peptide is SEQ ID NO:30; and (c) a fourth peptide, wherein the fourth peptide is SEQ ID NO:32, wherein each peptide comprises a T-cell epitope and a B-cell epitope.

In some embodiments, the antigenic composition comprises: (a) a first peptide comprising SEQ ID NO:25 or a variant thereof (b) a third peptide comprising SEQ ID NO:26 or a variant thereof and (c) a fourth peptide comprising SEQ ID NO:28 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof; (b) a third peptide comprising SEQ ID NO:31 or a variant thereof and (c) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; (b) a third peptide, wherein the third peptide is SEQ ID NO:31; and (c) a fourth peptide, wherein the fourth peptide is SEQ ID NO:32, wherein each peptide comprises a T-cell epitope and a B-cell epitope.

In some embodiments, the antigenic composition comprises: (a) a second peptide comprising SEQ ID NO:26 or a variant thereof (b) a third peptide comprising SEQ ID NO:27 or a variant thereof and (c) a fourth peptide comprising SEQ ID NO:28 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a second peptide comprising SEQ ID NO:30 or a variant thereof, (b) a third peptide comprising SEQ ID NO:31 or a variant thereof, and (c) a fourth peptide comprising SEQ ID NO:32 or a variant thereof, wherein each peptide comprises a T-cell epitope and a B-cell epitope. In some embodiments, the antigenic composition comprises: (a) a second peptide, wherein the second peptide is SEQ ID NO:30; (b) a third peptide, wherein the third peptide is SEQ ID NO:31; and (c) a fourth peptide, wherein the fourth peptide is SEQ ID NO:32, wherein each peptide comprises a T-cell epitope and a B-cell epitope.

In some embodiments, the antigenic composition comprises four or more labyrinthin-derived peptides. For example, in some embodiments, the antigenic composition comprises: (a) a first peptide comprising SEQ ID NO:25 or a variant thereof; (b) a second peptide comprising SEQ ID NO:26 or a variant thereof; (c) a third peptide comprising SEQ ID NO:27 or a variant thereof, and (d) a fourth peptide comprising SEQ ID NO:28 or a variant thereof, wherein each peptide comprises a T-cell epitope and a B-cell epitope. In some embodiments, each of the four or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof; (b) a second peptide comprising SEQ ID NO:30 or a variant thereof; (c) a third peptide comprising SEQ ID NO:31 or a variant thereof; and (d) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; (b) a second peptide, wherein the second peptide is SEQ ID NO:30; (c) a third peptide, wherein the third peptide is SEQ ID NO:31; and (d) a fourth peptide, wherein the fourth peptide is SEQ ID NO:32, wherein each peptide comprises a T-cell epitope and a B-cell epitope.

In some embodiments, wherein the antigenic composition comprises more than one labyrinthin-derived peptide, the ratio between each of the more than one labyrinthin-derived peptide may be selected to achieve a desired immunotherapeutic response. In some embodiments, the more than one labyrinthin-derived peptides, such as 2, 3, or 4 labyrinthin-derived peptides, are all provided in about the same amount in the antigenic composition. For example, in some embodiments, wherein the antigenic composition comprises more than one labyrinthin-derived peptide, the ratio of a first peptide to a second peptide is about 1:10 to about 10:1, such as about any of 1:9, 1:8, 1:7, 1:6, 1:5, 1:4, 1:3, 1:2, 1:1, 2:1, 3:1, 4:1, 5:1, 6:1, 7:1, 8:1, or 9:1. In some embodiments, wherein the antigenic composition comprises: (a) a first peptide, wherein the first peptide is SEQ ID NO:29; (b) a second peptide, wherein the second peptide is SEQ ID NO:30; (c) a third peptide, wherein the third peptide is SEQ ID NO:31; and (d) a fourth peptide, wherein the fourth peptide is SEQ ID NO:32, the ratio of the first peptide to the second peptide to the third peptide to the fourth peptide is about 1:1:1:1. In some embodiments, wherein the antigenic composition contains only the following peptides: (a) a first peptide, wherein the first peptide is SEQ ID NO:29; (b) a second peptide, wherein the second peptide is SEQ ID NO:30; (c) a third peptide, wherein the third peptide is SEQ ID NO:31; and (d) a fourth peptide, wherein the fourth peptide is SEQ ID NO:32, the ratio of the first peptide to the second peptide to the third peptide to the fourth peptide is about 1:1:1:1.

In some embodiments, the antigenic composition comprises one or more labyrinthin-derived peptides, wherein each of the one or more labyrinthin-derived peptides has a pI between about 3.4 to about 3.1, such as about 3.3 to about 3.15. In some embodiments, the antigenic composition comprises one or more labyrinthin-derived peptides, wherein each of the one or more labyrinthin-derived peptides has a pI of less than about 3.4, such as less than about any of 3.35, 3.3, 3.25, 3.2, 3.15, 3.1, 3.05, or 3. In some embodiments, the antigenic composition comprises one or more labyrinthin-derived peptides, wherein each of the one or more labyrinthin-derived peptides has a pI of any one of about 3.4, about 3.35, about 3.3, about 3.25, about 3.2, about 3.15, about 3.1, about 3.05, or about 3.

Nucleic Acid Compositions Comprising a Labyrinthin-Derived Peptide

In some embodiments, there is provided nucleic acid compositions comprising one or more nucleic acids encoding at least one of one or more labyrinthin-derived peptides comprised in the antigenic composition disclosed herein. In some embodiments, the nucleic acid composition comprises nucleic acids encoding at least two or more labyrinthin-derived peptides. In some embodiments, the nucleic acid composition comprises nucleic acids encoding at least three or more labyrinthin-derived peptides. In some embodiments, the nucleic acid composition comprises nucleic acids encoding four labyrinthin-derived peptides.

In some embodiments, the nucleic acid composition comprises one or more nucleic acids encoding a first peptide comprising SEQ ID NO:25 or a variant thereof. In some embodiments, the nucleic acid composition comprises one or more nucleic acids encoding a first peptide comprising SEQ ID NO:25. In some embodiments, the nucleic acid composition comprises one or more nucleic acids encoding a first peptide comprising SEQ ID NO:29 or a variant thereof. In some embodiments, the nucleic acid composition comprises one or more nucleic acids encoding a first peptide, wherein the first peptide is SEQ ID NO:29.

In some embodiments, the nucleic acid composition comprises one or more nucleic acids encoding a second peptide comprising SEQ ID NO:26 or a variant thereof. In some embodiments, the nucleic acid composition comprises one or more nucleic acids encoding a second peptide comprising SEQ ID NO:26. In some embodiments, the nucleic acid composition comprises one or more nucleic acids encoding a second peptide comprising SEQ ID NO:30 or a variant thereof. In some embodiments, the nucleic acid composition comprises one or more nucleic acids encoding a second peptide, wherein the second peptide is SEQ ID NO:30.

In some embodiments, the nucleic acid composition comprises one or more nucleic acids encoding a third peptide comprising SEQ ID NO:27 or a variant thereof. In some embodiments, the nucleic acid composition comprises one or more nucleic acids encoding a third peptide comprising SEQ ID NO:27. In some embodiments, the nucleic acid composition comprises one or more nucleic acids encoding a third peptide comprising SEQ ID NO:31 or a variant thereof. In some embodiments, the nucleic acid composition comprises one or more nucleic acids encoding a third peptide, wherein the third peptide is SEQ ID NO:31.

In some embodiments, the nucleic acid composition comprises one or more nucleic acids encoding a fourth peptide comprising SEQ ID NO:28 or a variant thereof. In some embodiments, the nucleic acid composition comprises one or more nucleic acids encoding a fourth peptide comprising SEQ ID NO:28. In some embodiments, the nucleic acid composition comprises one or more nucleic acids encoding a fourth peptide comprising SEQ ID NO:32 or a variant thereof. In some embodiments, the nucleic acid composition comprises one or more nucleic acids encoding a fourth peptide, wherein the fourth peptide is SEQ ID NO:32.

In some embodiments, the nucleic acid composition comprises one or more nucleic acid encoding at least one of one or more labyrinthin-derived peptides described herein, wherein at least one of the one or more nucleic acids is a non-naturally occurring sequence. In some embodiments, the nucleic acid composition comprises one or more nucleic acid encoding at least one of one or more labyrinthin-derived peptides described herein, wherein at least one of the one or more nucleic acids is conjugated, such as conjugated to a label.

Vaccine Compositions Comprising an Antigenic Composition

In some embodiments, there is provided vaccine compositions comprising: (a) an effective amount of the antigenic composition of any one of the antigenic compositions described herein; and (b) a pharmaceutically acceptable vehicle.

In some embodiments, the pharmaceutically acceptable vehicle is one or more of an aqueous suspension, an oily suspension, an emulsion, a liposome, a virosome, and a nanoparticle. In some embodiments, the pharmaceutically acceptable vehicle is selected from the group consisting of an aqueous suspension, an oily suspension, an emulsion, such as an oil-in-water emulsion, a liposome, a virosome, and a nanoparticle. In some embodiments, the pharmaceutically acceptable vehicle, or portion thereof, stabilizes an antigenic composition or portion thereof. In some embodiments, the pharmaceutically acceptable vehicle, or portion thereof, extends the circulating half-life of one or more labyrinthin-derived peptides, as compared to the circulating half-life of the one or more labyrinthin-derived peptides administered without the pharmaceutically acceptable vehicle.

In some embodiments, the pharmaceutically acceptable vehicle comprises an excipient. Excipients are known in the art. See, Mehmood, Y. et al., *Open Science J Pharm Pharm Sci,* 3, 2015, 19-27, which is hereby incorporated by reference in its entirety. In some embodiments, the excipient is one or more of a solvent, a co-solvent, a solubilizing agent, a wetting agent, a suspending agent, a emulsifying agent, a thickening agent, a chelating agent, an antioxidant agent, a reducing agent, an antimicrobial preservative, a buffer, a pH adjusting agent, a bulking agent, a protectant agent, and a tonicity agent. In some embodiments, the excipient comprises one or more of: a sugar, a saccharides, sucrose, lactose, trehalose, mannitol, sorbitol, glucose, rafinose, an amino acid, glycine, histidine, polyvinylpyrrolidone (PVP), sodium citrate, sodium chloride, potassium chloride, a phosphate, monopotassium phosphate, disodium phosphate, Tris base-65, Tris acetate, Tris HCl-65, dextrose, dextran, ficoll, gelatin, a starch, hydroxyethyl starch, magnesium stearate, polyethylene glycol (PEG), a vitamin, and water.

In some embodiments, the pharmaceutically acceptable vehicle comprises less than about 1% saline (NaCl), such as any of less than about 0.9%, 0.8%, 0.7%, 0.6%, 0.5%, 0.2%, 0.3%, 0.2%, or 0.1% saline. In some embodiments, the pharmaceutically acceptable vehicle comprises about 1% saline, 0.9% saline, 0.8% saline, 0.7% saline, 0.6% saline, 0.5% saline, 0.2% saline, 0.3% saline, 0.2% saline, or 0.1% saline. In some embodiments, the vaccine composition comprises an effective amount of an antigenic composition described herein, wherein the antigenic composition is reconstituted with a pharmaceutically acceptable vehicle comprising less than about 1% saline, such as any of less than about 0.9%, 0.8%, 0.7%, 0.6%, 0.5%, 0.2%, 0.3%, 0.2%, or 0.1% saline. In some embodiments, the vaccine composition comprises an effective amount of an antigenic composition described herein, wherein the antigenic composition is reconstituted with a pharmaceutically acceptable vehicle comprising about 1% saline, saline, 0.9% saline, 0.8% saline, 0.7% saline, 0.6% saline, 0.5% saline, 0.2% saline, 0.3% saline, 0.2% saline, or 0.1% saline.

In some embodiments, the pharmaceutically acceptable vehicle comprises one or more of: a lipid, a lipopolysaccharide, a monophosphoryl lipid (A), a lipopolysaccharide, and 3-O-desacyl-4-monophosphoryl lipid A.

In some embodiments, the pharmaceutically acceptable vehicle comprises an adjuvant. In some embodiments, the pharmaceutically acceptable vehicle comprises an immune-enhancing adjuvant. In some embodiments, the pharmaceutically acceptable vehicle comprises an immune-enhancing amount of an adjuvant, such as an immune-enhancing adjuvant. Adjuvants, including immune-enhancing adjuvants, are known in the art. In some embodiments, the adjuvant is Granulocyte-Macrophage Colony Stimulating Factor (GM-CSF). In some embodiments, the adjuvant is GM-CSF of the organism for which administration of the vaccine in intended, e.g., human GM-CSF. In some embodiments, the adjuvant comprises a saponin. See, U.S. Pat. Nos. 5,583,112, 5,057,540, 7,858,589, and 7,939,084; and Alving, C. R. et al., *Curr Opin Immunol*, 2012, 24, 310-315, which are hereby incorporated by reference in their entirety. In some embodiments, the saponin is QS-21 (Quillaja saponaria Molina, fraction 21). In some embodiments, the adjuvant comprises 3-O-desacyl-4'-monophosphoryl lipid A (MPL). In some embodiments, the adjuvant comprises AS01B, which comprises QS-21, MPL, and liposomes comprising DOPC (dioleoyl phosphatidylcholine) and cholesterol in phosphate buffer. In some embodiments, the adjuvant comprises AS04. In some embodiments, the adjuvant comprises AS02A. In some embodiments, the adjuvant comprises AS01E.

In some embodiments, the vaccine composition comprises any one of the antigenic compositions described herein, wherein a labyrinthin-derived peptide comprised therein is in a salt form with a pharmaceutically acceptable salt. Pharmaceutically acceptable salts are known in the art. See, Berge et al., *J Pharm Sci,* 66, 1977, 1-19, which is hereby incorporated by reference in its entirety. In some embodiments, the pharmaceutically acceptable salt is sodium chloride. In some embodiments, the pharmaceutically acceptable salt is an acetate salt. In some embodiments, the pharmaceutically acceptable salt is sodium acetate. In some embodiments, the pharmaceutically acceptable salt is potassium chloride.

In some embodiments, the pharmaceutically acceptable vehicle comprises a pharmaceutically acceptable acid. In some embodiments, the pharmaceutically acceptable acid is acetic acid. In some embodiments, the concentration of a pharmaceutically acceptable acid in a vaccine composition is less than or about 1%, such as less than or about 0.9%, 0.8%, 0.7%, 0.6%, 0.5%, 0.4%, 0.3%, 0.2%, or 0.1%.

In some embodiments, wherein the vaccine composition comprises more than one labyrinthin-derived peptide, the ratio between each of the more than one labyrinthin-derived peptide may be selected to achieve a desired immunotherapeutic response. In some embodiments, the more than one labyrinthin-derived peptides, such as 2, 3, or 4 labyrinthin-derived peptides, are all provided in about the same amount in the vaccine composition. For example, in some embodiments, wherein the vaccine composition comprises more than one labyrinthin-derived peptide, the ratio of a first peptide to a second peptide is about 1:10 to about 10:1, such as about any of 1:9, 1:8, 1:7, 1:6, 1:5, 1:4, 1:3, 1:2, 1:1, 2:1, 3:1, 4:1, 5:1, 6:1, 7:1, 8:1, or 9:1. In some embodiments, wherein the vaccine composition comprises: (a) a first peptide, wherein the first peptide is SEQ ID NO:29; (b) a second peptide, wherein the second peptide is SEQ ID NO:30; (c) a third peptide, wherein the third peptide is SEQ ID NO:31; and (d) a fourth peptide, wherein the fourth peptide is SEQ ID NO:32, the ratio of the first peptide to the second peptide to the third peptide to the fourth peptide is about 1:1:1:1. In some embodiments, wherein the vaccine composition contains only the following peptides: (a) a first peptide, wherein the first peptide is SEQ ID NO:29; (b) a second peptide, wherein the second peptide is SEQ ID NO:30; (c) a third peptide, wherein the third peptide is SEQ ID NO:31; and (d) a fourth peptide, wherein the fourth peptide is SEQ ID NO:32, the ratio of the first peptide to the second peptide to the third peptide to the fourth peptide is about 1:1:1:1.

In some embodiments, the vaccine composition comprises an effective amount of an antigenic composition of any one of the antigenic compositions described herein, wherein the effective amount is between about 1 µg and about 500 µg. In some embodiments, the vaccine composition comprises an effective amount of an antigenic composition of any one of the antigenic compositions described herein, wherein the effective amount is at least about 1 µg of total peptide, such as at least about any of 2 µg, 3 µg, 4 µg, 5 µg, 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 175 µg, 200 µg, 225 µg, 250 µg, 275 µg, 300 µg, 325 µg, 350 µg, 375 µg, 400 µg, 425 µg, 450 µg, 475 µg, or 500 µg.

In some embodiments, the vaccine composition comprises an effective amount of an antigenic composition of any one of the antigenic compositions described herein, wherein the effective amount is between about 1 µg and about 1000 µg. In some embodiments, the vaccine composition comprises an effective amount of an antigenic composition of any one of the antigenic compositions described herein, wherein the effective amount is at least about 1 µg of total peptide, such as at least about any of 2 µg, 3 µg, 4 µg, 5 µg, 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 550 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, or 1000 µg.

In some embodiments, wherein the vaccine composition comprises more than one labyrinthin-derived peptide, each of the more than one labyrinthin-derived peptide is present in the vaccine composition in an amount of about 0.1 µg to about 500 µg. In some embodiments, wherein the vaccine composition comprises more than one labyrinthin-derived peptide, each of the more than one labyrinthin-derived peptide is present in the vaccine composition in an amount of about any of 0.1 µg, 0.5 µg, 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 175 µg, 200 µg, 225 µg, 250 µg, 275 µg, 300 µg, 325 µg, 350 µg, 375 µg, 400 µg, 425 µg, 450 µg, 475 µg, or 500 µg.

In some embodiments, the vaccine composition has a pH of about 5 to about 8.5, such as any of about 5.5 to about 7, about 6 to about 6.75, about 6.25 to about 6.75, about 6 to about 7, or about 6.5 to about 7.

In some embodiments, the vaccine composition has a pH of about any of 5, 5.25, 5.5, 5.75, 6, 6.25, 6.5, 6.75, 7, 7.25, 7.5, 7.75, 8, 8.25, or 8.5.

In some embodiments, the vaccine composition comprises another therapeutic agent, such as an immune checkpoint inhibitor.

In some embodiments, the vaccine composition is pharmaceutically acceptable. In some embodiments, the vaccine composition is pharmaceutically sterile.

In some embodiments, the vaccine composition comprises: (i) an effective amount of an antigenic composition described herein; and (ii) a pharmaceutically acceptable vehicle. In some embodiments, the vaccine composition comprises: (i) an effective amount of an antigenic composition described herein; and (ii) a pharmaceutically acceptable vehicle comprising an adjuvant, such as GM-CSF. In some embodiments, the antigenic composition comprises one or more labyrinthin-derived peptides, wherein each labyrinthin-derived peptide comprises one or more of a T-cell epitope and a B-cell epitope. In some embodiments, each of the one or more labyrinthin-derived peptides comprises a T-cell epitope and a B-cell epitope. In some embodiments, the one or more labyrinthin-derived peptides are between 8 and 25 amino acids in length. In some embodiments, the one or more labyrinthin-derived peptides are substantially homologous to a portion of labyrinthin. In some embodiments, each of the one or more labyrinthin-derived peptides comprises a non-terminal proline residue.

In some embodiments, the vaccine composition comprises: (i) an effective amount of an antigenic composition, wherein the antigenic composition comprises one or more labyrinthin-derived peptides selected from the group comprising: (a) a first peptide comprising SEQ ID NO:25 or a variant thereof, (b) a second peptide comprising SEQ ID NO:26 or a variant thereof; (c) a third peptide comprising SEQ ID NO:27 or a variant thereof, and (d) a fourth peptide comprising SEQ ID NO:28 or a variant thereof, and wherein each peptide comprises a T-cell epitope and a B-cell epitope; and (ii) a pharmaceutically acceptable vehicle. For example, in some embodiments, the antigenic composition of a vaccine composition comprises a first peptide comprising SEQ ID NO:25 or a variant thereof, wherein the first peptide comprises a T-cell epitope and a B-cell epitope. In some embodiments, the second peptide is between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the antigenic composition comprises a first peptide comprising SEQ ID NO:29 or a variant thereof, wherein the first peptide comprises a T-cell epitope and a B-cell epitope. In some embodiments, the antigenic composition comprises a first peptide, wherein the first peptide is SEQ ID NO:29, and wherein the first peptide comprises a T-cell epitope and a B-cell epitope. In some embodiments, each peptide of the antigenic composition activates T-cell and B-cell adaptive immune responses. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the pharmaceutically acceptable vehicle comprises a saponin. In some embodiments, the vaccine composition comprises GM-CSF.

In some embodiments, the antigenic composition of a vaccine composition comprises a second peptide comprising SEQ ID NO:26 or a variant thereof, wherein the second peptide comprises a T-cell epitope and a B-cell epitope. In some embodiments, the second peptide is between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the antigenic composition comprises a second peptide comprising SEQ ID NO:30 or a variant thereof, wherein the second peptide comprises a T-cell epitope and a B-cell epitope. In some embodiments, the antigenic composition comprises a second peptide, wherein the second peptide is SEQ ID NO:30, and wherein the second peptide comprises a T-cell epitope and a B-cell epitope. In some embodiments, each peptide of the antigenic composition activates T-cell and B-cell adaptive immune responses. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the pharmaceutically acceptable vehicle comprises a saponin. In some embodiments, the vaccine composition comprises GM-CSF.

In some embodiments, the antigenic composition of a vaccine composition comprises a third peptide comprising SEQ ID NO:27 or a variant thereof, wherein the third peptide comprises a T-cell epitope and a B-cell epitope. In some embodiments, the third peptide is between 21 and 24 amino acids in length, such as 22 or 23 amino acids in length. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises a third peptide comprising SEQ ID NO:31 or a variant thereof, wherein the third peptide comprises a T-cell epitope and a B-cell epitope. In some embodiments, the antigenic composition comprises a third peptide, wherein the third peptide is SEQ ID NO:31, and wherein the third peptide comprises a T-cell epitope and a B-cell epitope. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the pharmaceutically acceptable vehicle comprises a saponin. In some embodiments, the vaccine composition comprises GM-CSF.

In some embodiments, the antigenic composition of a vaccine composition comprises a fourth peptide comprising SEQ ID NO:28 or a variant thereof, wherein the fourth peptide comprises a T-cell epitope and a B-cell epitope. In some embodiments, the fourth peptide is between 21 and 24 amino acids in length, such as 22 or 23 amino acids in length. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises a fourth peptide comprising SEQ ID NO:32 or a variant thereof, wherein the fourth peptide comprises a T-cell epitope and a B-cell epitope. In some embodiments, the antigenic composition comprises a fourth peptide, wherein the fourth peptide is SEQ ID NO:32, and wherein the fourth peptide comprises a T-cell epitope and a B-cell epitope. In some embodiments, each peptide of the antigenic composition activates T-cell and B-cell adaptive immune responses. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises two or more labyrinthin-derived peptides. For example, in some embodiments, the antigenic composition of a vaccine composition comprises: (a) a first peptide comprising SEQ ID NO:25 or a variant thereof; and (b) a second peptide comprising SEQ ID NO:26 or a variant thereof, wherein each peptide comprises a T-cell epitope and a B-cell epitope. In some embodiments, each of the two or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the antigenic composition comprises: (a) a first peptide comprising SEQ ID NO:29 or a variant thereof and (b) a second peptide comprising SEQ ID NO:30 or a variant thereof, wherein each peptide comprises a T-cell epitope and a B-cell epitope. In some embodiments, the antigenic composition comprises: (a) a first peptide, wherein the first peptide is SEQ ID NO:29; and (b) a second peptide, wherein the second peptide is SEQ ID NO:30, wherein each peptide comprises a T-cell epitope and a B-cell epitope. In some embodiments, each peptide of the antigenic composition activates T-cell and B-cell adaptive immune responses. In some embodiments, the effective amount of an antigenic composition in a vaccine composition is between about 0.1

μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises: (a) a first peptide comprising SEQ ID NO:25 or a variant thereof and (b) a third peptide comprising SEQ ID NO:27 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises: (a) a first peptide comprising SEQ ID NO:29 or a variant thereof; and (b) a third peptide comprising SEQ ID NO:31 or a variant thereof, wherein each peptide comprises a T-cell epitope and a B-cell epitope. In some embodiments, the antigenic composition comprises: (a) a first peptide, wherein the first peptide is SEQ ID NO:29; and (b) a third peptide, wherein the third peptide is SEQ ID NO:31, wherein each peptide comprises a T-cell epitope and a B-cell epitope. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises: (a) a first peptide comprising SEQ ID NO:25 or a variant thereof; and (b) a fourth peptide comprising SEQ ID NO:28 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof, and (b) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; and (b) a fourth peptide, wherein the fourth peptide is SEQ ID NO:32, wherein each peptide comprises a T-cell epitope and a B-cell epitope. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises: (a) a second peptide comprising SEQ ID NO:26 or a variant thereof; and (b) a third peptide comprising SEQ ID NO:27 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises: (a) a second peptide comprising SEQ ID NO:30 or a variant thereof, and (b) a third peptide comprising SEQ ID NO:31 or a variant thereof, wherein each peptide comprises a T-cell epitope and a B-cell epitope. In some embodiments, the antigenic composition comprises: (a) a second peptide, wherein the second peptide is SEQ ID NO:30; and (b) a third peptide, wherein the third peptide is SEQ ID NO:31, wherein each peptide comprises a T-cell epitope and a B-cell epitope. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises: (a) a second peptide comprising SEQ ID NO:26 or a variant thereof; and (b) a fourth peptide comprising SEQ ID NO:28 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a second peptide comprising SEQ ID NO:30 or a variant thereof; and (b) a fourth peptide comprising SEQ ID NO:32 or a variant thereof, wherein each peptide comprises a T-cell epitope and a B-cell epitope. In some embodiments, the antigenic composition comprises: (a) a second peptide, wherein the second peptide is SEQ ID NO:30; and (b) a fourth peptide, wherein the fourth peptide is SEQ ID NO:32, wherein each peptide comprises a T-cell epitope and a B-cell epitope. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises: (a) a third peptide comprising SEQ ID NO:27 or a variant thereof; and (b) a fourth peptide comprising SEQ ID NO:28 or a variant thereof, wherein each peptide comprises a T-cell epitope and a B-cell epitope. In some embodiments, the two or more labyrinthin-derived peptides are between 21 and 24 amino acids in length, such as 22 or 23 amino acids in length. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a third peptide comprising SEQ ID NO:31 or a variant thereof; and (b) a fourth peptide comprising SEQ ID NO:32 or a variant thereof, wherein each peptide comprises a T-cell epitope and a B-cell epitope. In some embodiments, the antigenic composition comprises: (a) a third peptide, wherein the third peptide is SEQ ID NO:31; and (b) a fourth peptide, wherein the fourth peptide is SEQ ID NO:32, wherein each peptide comprises a T-cell epitope and a B-cell epitope. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the pharmaceutically acceptable vehicle comprises a saponin. In some embodiments, the vaccine composition comprises GM-CSF.

In some embodiments, the antigenic composition of a vaccine composition comprises three or more labyrinthin-derived peptides. For example, in some embodiments, the antigenic composition comprises: (a) a first peptide comprising SEQ ID NO:25 or a variant thereof; (b) a second peptide comprising SEQ ID NO:26 or a variant thereof; and (c) a third peptide comprising SEQ ID NO:27 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the antigenic composition comprises: (a) a first peptide comprising SEQ ID NO:29 or a variant thereof, (b) a second peptide comprising SEQ ID NO:30 or a variant thereof, and (c) a third peptide comprising SEQ ID NO:31 or a variant thereof, wherein each peptide comprises a T-cell epitope and a B-cell epitope. In some embodiments, the antigenic composition comprises: (a) a first peptide, wherein the first peptide is SEQ ID NO:29; (b) a second peptide, wherein the second peptide is SEQ ID NO:30; and (c) a third peptide, wherein the third peptide is SEQ ID NO:31, wherein each peptide comprises a T-cell epitope and a B-cell epitope. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the pharmaceutically acceptable vehicle comprises a saponin. In some embodiments, the vaccine composition comprises GM-CSF.

In some embodiments, the antigenic composition of a vaccine composition comprises: (a) a first peptide comprising SEQ ID NO:25 or a variant thereof; (b) a second peptide comprising SEQ ID NO:26 or a variant thereof, and (c) a fourth peptide comprising SEQ ID NO:28 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof; (b) a second peptide comprising SEQ ID NO:30 or a variant thereof; and (c) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; (b) a second peptide, wherein the second peptide is SEQ ID NO:30; and (c) a fourth peptide, wherein the fourth peptide is SEQ ID NO:32, wherein each peptide comprises a T-cell epitope and a B-cell epitope. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises: (a) a first peptide comprising SEQ ID NO:25 or a variant thereof; (b) a third peptide comprising SEQ ID NO:26 or a variant thereof; and (c) a fourth peptide comprising SEQ ID NO:28 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof (b) a third peptide comprising SEQ ID NO:31 or a variant thereof and (c) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; (b) a third peptide, wherein the third peptide is SEQ ID NO:31; and (c) a fourth peptide, wherein the fourth peptide is SEQ ID NO:32, wherein each peptide comprises a T-cell epitope and a B-cell epitope. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the pharmaceutically acceptable vehicle comprises a saponin. In some embodiments, the vaccine composition comprises GM-CSF.

In some embodiments, the antigenic composition of a vaccine composition comprises: (a) a second peptide comprising SEQ ID NO:26 or a variant thereof; (b) a third peptide comprising SEQ ID NO:27 or a variant thereof, and (c) a fourth peptide comprising SEQ ID NO:28 or a variant thereof, wherein each peptide comprises a T-cell epitope and a B-cell epitope. In some embodiments, each of the three or more labyrinthin-derived peptides are between 21 and 24 amino acids in length, such as 22 or 23 amino acids in length. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a second peptide comprising SEQ ID NO:30 or a variant thereof; (b) a third peptide comprising SEQ ID NO:31 or a variant thereof, and (c) a fourth peptide comprising SEQ ID NO:32 or a variant thereof, wherein each peptide comprises a T-cell epitope and a B-cell epitope. In some embodiments, the antigenic composition comprises: (a) a second peptide, wherein the second peptide is SEQ ID NO:30; (b) a third peptide, wherein the third peptide is SEQ ID NO:31; and (c) a fourth peptide, wherein the fourth peptide is SEQ ID NO:32, wherein each peptide comprises a T-cell epitope and a B-cell epitope. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the pharmaceutically acceptable vehicle comprises a saponin. In some embodiments, the vaccine composition comprises GM-CSF.

In some embodiments, the antigenic composition of a vaccine composition comprises four or more labyrinthin-derived peptides. For example, in some embodiments, the antigenic composition of a vaccine composition comprises: (a) a first peptide comprising SEQ ID NO:25 or a variant thereof; (b) a second peptide comprising SEQ ID NO:26 or a variant thereof, (c) a third peptide comprising SEQ ID NO:27 or a variant thereof, and (d) a fourth peptide comprising SEQ ID NO:28 or a variant thereof, wherein each peptide comprises a T-cell epitope and a B-cell epitope. In some embodiments, each of the four or more labyrinthin-derived peptides are between 21 and 24 amino acids in length, such as 22 or 23 amino acids in length. In some embodiments, the first peptide comprising SEQ ID NO:25 or a variant thereof comprises SEQ ID NO:29 or a variant thereof. In some embodiments, the first peptide comprising SEQ ID NO:25 or a variant thereof has a sequence similarity of at least about 90% similarity, such as at least about any of 92% similarity, 95% similarity, or 97% similarity, to a portion of labyrinthin (SEQ ID NO:1). In some embodiments, the first peptide comprising SEQ ID NO:25 is SEQ ID NO:29. In some embodiments, the first peptide comprising SEQ ID NO:25 or a variant thereof is conjugated. In some embodiments, the second peptide comprising SEQ ID NO:26 or a variant thereof comprises SEQ ID NO:30 or a variant thereof. In some embodiments, the second peptide comprising SEQ ID NO:30 or a variant thereof has a sequence similarity of at least about 90% similarity, such as at least about any of 92% similarity, 95% similarity, or 97% similarity, to a portion of labyrinthin (SEQ ID NO:1). In some embodiments, the second peptide comprising SEQ ID NO:26 is SEQ ID NO:30. In some embodiments, the second peptide comprising SEQ ID NO:26 or a variant thereof is conjugated. In some embodiments, the third peptide comprising SEQ ID NO:27 or a variant thereof comprises SEQ ID NO:31 or a variant thereof. In some embodiments, the third peptide comprising SEQ ID NO:27 or a variant thereof has a sequence similarity of at least about 90% similarity, such as at least about any of 92% similarity, 95% similarity, or 97% similarity, to a portion of labyrinthin (SEQ ID NO:1). In some embodiments, the third peptide comprising SEQ ID NO:27 is SEQ ID NO:31. In some embodiments, the third peptide comprising SEQ ID NO:27 or a variant thereof is conjugated. In some embodiments, the fourth peptide comprising SEQ ID NO:28 or a variant thereof comprises SEQ ID NO:32 or a variant thereof. In some embodiments, the fourth peptide comprising SEQ ID NO:28 or a variant thereof has a sequence similarity of at least about 90% similarity, such as at least about any of 92% similarity, 95% similarity, or 97% similarity, to a portion of labyrinthin (SEQ ID NO:1). In some embodiments, the fourth peptide comprising SEQ ID NO:28 is SEQ ID NO:32. In some embodiments, the fourth peptide comprising SEQ ID NO:28 or a variant thereof is conjugated. In some embodiments, the antigenic composition comprises: (a) a first peptide comprising SEQ ID NO:29 or a variant thereof, (b) a second peptide comprising SEQ ID NO:30 or a variant thereof, (c) a third peptide comprising SEQ ID NO:31 or a variant thereof, and (d) a fourth peptide comprising SEQ ID NO:32 or a variant thereof, wherein each peptide comprises a T-cell epitope and a B-cell epitope. In some embodiments, the antigenic composition comprises: (a) a first peptide, wherein the first peptide is SEQ ID NO:29; (b) a second peptide, wherein the second peptide is SEQ ID NO:30; (c) a third peptide, wherein the third peptide is SEQ ID NO:31; and (d) a fourth peptide, wherein the fourth peptide is SEQ ID NO:32, wherein each peptide comprises a T-cell epitope and a B-cell epitope. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the pharmaceutically acceptable vehicle comprises a saponin. In some embodiments, the vaccine composition comprises GM-CSF. In some embodiments, the vaccine composition is LabVax 3(22)-23.

In some embodiments, the vaccine composition comprises one or more labyrinthin-derived peptides selected from the group comprising: (a) a first peptide comprising SEQ ID NO:25 or a variant thereof, (b) a second peptide comprising SEQ ID NO:26 or a variant thereof; (c) a third peptide comprising SEQ ID NO:27 or a variant thereof, and (d) a fourth peptide comprising SEQ ID NO:28 or a variant thereof. In some embodiments, the vaccine composition comprises: (a) a first peptide comprising SEQ ID NO:25 or a variant thereof; (b) a second peptide comprising SEQ ID NO:26 or a variant thereof, (c) a third peptide comprising SEQ ID NO:27 or a variant thereof, and (d) a fourth peptide comprising SEQ ID NO:28 or a variant thereof. In some embodiments, the vaccine composition comprises: (a) a first peptide comprising SEQ ID NO:25 or a variant thereof (b) a second peptide comprising SEQ ID NO:26 or a variant thereof (c) a third peptide comprising SEQ ID NO:27 or a variant thereof and (d) a fourth peptide comprising SEQ ID NO:28 or a variant thereof, wherein these are the only four labyrinthin-derived peptides in the vaccine composition. In some embodiments, the labyrinthin-derived peptides are between 21 and 24 amino acids in length, such as 22 or 23 amino acids in length. In some embodiments, the vaccine composition comprising a peptide comprising SEQ ID NO:25 or a variant thereof comprises SEQ ID NO:29 or a variant thereof. In some embodiments, the vaccine composition comprising a peptide comprising SEQ ID NO:26 or a variant thereof comprises SEQ ID NO:30 or a variant thereof. In some embodiments, the vaccine composition comprising a peptide comprising SEQ ID NO:27 or a variant thereof comprises SEQ ID NO:31 or a variant thereof. In some embodiments, the vaccine composition comprising a peptide comprising SEQ ID NO:28 or a variant thereof comprises SEQ ID NO:32 or a variant thereof. In some embodiments, the vaccine composition comprises: (a) a first peptide comprising SEQ ID NO:29 or a variant thereof (b) a second peptide comprising SEQ ID NO:30 or a variant thereof (c) a third peptide comprising SEQ ID NO:31 or a variant thereof and (d) a fourth peptide comprising SEQ ID NO:32 or a variant thereof, wherein these are the only four labyrinthin-derived peptides in the vaccine composition. In some embodiments, the vaccine composition consists essentially of: (a) a first peptide comprising SEQ ID NO:29 or a variant thereof (b) a second peptide comprising SEQ ID NO:30 or a variant thereof (c) a third peptide comprising SEQ ID NO:31 or a variant thereof and (d) a fourth peptide comprising SEQ ID NO:32 or a variant thereof, wherein these are the only four labyrinthin-derived peptides in the vaccine composition. In some embodiments, the labyrinthin-derived peptide comprises a T-cell epitope and/or a B-cell epitope. In some embodiments, the effective amount of an antigenic composition in a vaccine composition is between about 0.1 µg and about 1000 µg, such as about 75 µg and about 150 µg, such as about 100 µg. In some embodiments, the vaccine composition comprises GM-CSF. In some embodiments, the vaccine composition is LabVax 3(22)-23.

In some embodiments, the vaccine composition comprises four labyrinthin-derived peptides, wherein the four labyrinthin-derived peptides are SEQ ID NOS:29-32, wherein these are the only four labyrinthin-derived peptides in the vaccine composition, wherein each peptide is present at an amount of 100 µg, and wherein the volume of the vaccine is about 0.1 mL. In some embodiments, the vaccine composition is LabVax 3(22)-23. In some embodiments, LabVax 3(22)-23 further comprises GM-CSF.

Kits, Medicines, and Compositions Thereof

The present disclosure, in some aspects, provides compositions comprising an antigenic composition disclosed herein, including kits, medicines, and compositions (such as pharmaceutical compositions and unit dosages) thereof. In some aspects, the present disclosure provides vaccine compositions comprising an antigenic composition disclosed herein, including kits, medicines, and compositions (such as pharmaceutical compositions and unit dosages) thereof.

In some embodiments, kits of the present disclosure may include one or more containers comprising an antigenic composition and/or a vaccine composition described herein (or a unit dosage and/or an article of manufacture thereof). In some embodiments, the kit further comprises one or more containers comprising another agent (or a unit dosage and/or an article of manufacture thereof), such as an adjuvant, including immune-effective adjuvants, such as GM-CSF. In some embodiments, the kit further comprises instructions for use in accordance with any of the methods disclosed herein. The kit may also comprise a description of criteria for selection of an individual suitable for treatment with any of the methods disclosed herein. Instructions supplied in the kits disclosed herein are typically written instructions on a label or package insert (e.g., a paper sheet included in the kit), but machine-readable instructions (e.g., instructions carried on a magnetic or optical storage disk) are also acceptable.

In some embodiments, the composition comprising an antigenic composition described herein, such as a vaccine composition, may be present in separate containers or in a single container.

In some embodiments, the kits of the present disclosure are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

Also provided in the present disclosure are medicines and compositions (such as unit dosages) useful for the methods described herein. For example, in some embodiments, there is provided use of a composition comprising an antigenic composition, such as a vaccine composition, for a treatment of a cancer in an individual in need thereof.

Methods of Use Thereof

The present disclosure, in some aspects, provides methods of use of the vaccine compositions descried herein. In some aspects, the present disclosure provides a method for treating a cancer in an individual in need thereof, the method comprising administering to the individual a vaccine composition described herein. In other aspects, the present disclosure provides a method for preventing a cancer in an individual in need thereof, the method comprising administering to the individual a vaccine composition described herein. In some embodiments, the cancer is a labyrinthin-positive cancer. In some embodiments, the cancer is an adenocarcinoma, such as a labyrinthin-positive adenocarcinoma.

In some embodiment, the method for treating a cancer comprises administering to the individual a vaccine composition, wherein the vaccine composition comprises: (i) an effective amount of an antigenic composition comprising one or more labyrinthin-derived peptides, the labyrinthin-derived peptide comprising a sequence selected from SEQ ID NO:2-32, or a variant thereof and (ii) a pharmaceutically acceptable vehicle. In some embodiments, the labyrinthin-derived peptide comprising a sequence selected from SEQ ID NO:2-32 (Table 2), or variant thereof, comprises a flanking amino acid sequence on one or more terminal sides of the core sequence provided in SEQ ID NO:2-32.

In some embodiment, the method for preventing a cancer comprises administering to the individual a vaccine composition, wherein the vaccine composition comprises: (i) an effective amount of an antigenic composition comprising one or more labyrinthin-derived peptides, the labyrinthin-derived peptide comprising a sequence selected from SEQ ID NO:2-32, or a variant thereof and (ii) a pharmaceutically acceptable vehicle. In some embodiments, the labyrinthin-derived peptide comprising a sequence selected from SEQ ID NO:2-32 (Table 2), or variant thereof, comprises a flanking amino acid sequence on one or more terminal sides of the core sequence provided in SEQ ID NO:2-32.

In some embodiments, the method for treating a cancer in an individual comprises administering to the individual a vaccine composition described herein, wherein the labyrinthin status of the cancer is used as a basis for selecting the individual for the treatment. In some embodiments, the labyrinthin status of the cancer is indicative of labyrinthin expression (such as labyrinthin overexpression as compared to a control, e.g., a healthy or non-cancerous tissue of the individual) in the cancer. In some embodiments, the labyrinthin status of the cancer is indicative of labyrinthin presentation on a cell surface of the cancer. In some embodiments, the individual is selected for treatment when a cancer sample from the individual shows that about 10% or greater, such as at least about any of 15%, 20%, 25%, 30%, 35%, 40%, 45%, 50%, 55%, 60%, 65%, 75%, 80%, 85%, 90%, or 95%, of cancerous cells in the sample are positive for labyrinthin, such as determined using an immunohisto-chemical (IHC) technique. In some embodiments, the individual is selected for treatment when a cancer sample from the individual shows that about 10% or greater, such as at least about any of 15%, 20%, 25%, 30%, 35%, 40%, 45%, 50%, 55%, 60%, 65%, 75%, 80%, 85%, 90%, or 95%, of a subpopulation of cancerous cells in the sample, such as cells at the periphery of a tumor, are positive for labyrinthin, such as determined using an immunohistochemical (IHC) technique.

In some embodiments, disclosed herein is a method for treating a labyrinthin-positive cancer in an individual, the method comprising administering to the individual a vaccine composition, wherein the vaccine composition comprises an effective amount of an antigenic composition comprising: (a) a first peptide comprising SEQ ID NO:29 or a variant thereof, (b) a second peptide comprising SEQ ID NO:30 or a variant thereof; (c) a third peptide comprising SEQ ID NO:31 or a variant thereof; and (d) a fourth peptide comprising SEQ ID NO:32 or a variant thereof. In some embodiments, each peptide comprises a T-cell epitope and a B-cell epitope. In some embodiments, the effective amount of an antigenic composition in a vaccine composition is between about 0.1 µg and about 1000 µg, such as about 75 µg and about 150 µg, such as about 100 µg. In some embodiments, the effective amount of an antigenic composition of a vaccine composition is between about 25 µg and about 75 µg. In some embodiments, the vaccine composition is LabVax 3(22)-23. In some embodiments, the method further comprises selecting the individual for the treatment based on a labyrinthin status of the cancer being indicative of a labyrinthin-positive cancer. In some embodiments, the labyrinthin status of the cancer is indicative of a labyrinthin-positive cancer when about 10% or greater of cancerous cells in a sample from the individual are positive for labyrinthin, such as determined using an immunohisto-chemical (IHC) technique. In some embodiments, the laby-rinthin-positive cancer is an adenocarcinoma.

The methods disclosed herein may comprise administering to the individual a plurality of doses of the vaccine compositions described herein over a period of time. For example, the vaccine compositions described herein may be repeatedly administered to the individual over a period of time until the individual develops an adequate immunogenic response to components of the vaccine composition. In some embodiments, the method comprises administering a vaccine composition to an individual in need thereof, wherein the individual receives about 1 to about 10 separate administrations of the vaccine composition. In some embodiments, the method comprises administering a vaccine composition to an individual in need thereof, wherein the individual receives 1, 2, 3, 4, 5, 6, 7, 8, 9, or 10 separate administrations of the vaccine composition. In some embodiments, the method comprises administering a vaccine composition to an individual in need thereof, wherein the individual receives at least 1, such as at least any of 2, 3, 4, 5, 6, 7, 8, 9, or 10, separate administrations of the vaccine composition. In some embodiments, the method comprises administering a vaccine composition to an individual in need thereof, wherein the individual receives at least 1 separate administrations of the vaccine composition over a period of about 6 months. In some embodiments, the method comprises administering a vaccine composition to an individual in need thereof, wherein the individual receives at least 4 separate administrations of the vaccine composition over a period of about 6 months. In some embodiments, the method comprises administering a vaccine composition to an individual in need thereof, wherein the individual receives at least 10 separate administrations of the vaccine composition over a period of about 6 months. In some embodiments, the separate administrations of a vaccine composition are spaced about 1 week apart. In some embodiments, the method comprises administering a vaccine composition to an individual in need thereof, such as via intradermal administration, wherein the individual receives at least 5 separate administrations of the vaccine composition over a period of 12 weeks. In some embodiments, the method comprises administering a vaccine composition to an individual in need thereof, such as via intradermal administration, wherein the individual receives at least 7 separate administrations of the vaccine composition over a period of 36 weeks. In some embodiment, one or more additional vaccinations are administered to the individual in need thereof. In some embodiments, the method comprises administering a vaccine composition to an individual, wherein subsequent administrations of the vaccine composition to the individual are adjusted (such as via the frequency of administrations, spacing of time between administrations, or dosage amount). In some embodiments, the dosing frequency and or dosage amount of a vaccine composition is adjusted over the course of the treatment, based on the judgment of the administering physician.

The vaccine compositions may be administered via numerous administration routes. For example, the agents described herein can be administered to an individual (such as human) parenterally, including intravenous, intra-arterial, intraperitoneal, intrapulmonary, oral, inhalation, intravesicular, intramuscular, intra-tracheal, subcutaneous, intraocular, intrathecal, intradermal, or transdermal. In some embodiments, the agents described herein, such as a vaccine composition, are administered intradermally, such as via an intradermal injection. In some embodiments, the vaccine compositions described herein are administered intradermally, wherein each injection in a series of vaccinations is administered in a different site (e.g., at least 3 cm away from a previous injection). In some embodiments, wherein the route of administration is intradermal administration, the administration needle or syringe is held in place for at least about 3 minutes to about 5 minutes following injection of the vaccine composition.

In some embodiments, the method for treating and/or preventing a cancer in an individual further comprises administering to the individual another agent. In some embodiments, the other agent is an adjuvant. In some embodiments, the adjuvant is Granulocyte-Macrophage Colony Stimulating Factor (GM-CSF). In some embodiments, the adjuvant is GM-CSF of the organism for which administration of the vaccine in intended, e.g., human GM-CSF. In some embodiments, the method comprises administering GM-CSF separately from the vaccine composition. In some embodiments, the other agent is a chemotherapeutic agent. In some embodiments, the GM-CSF is administered separately from the vaccine composition, such as about 45 minutes to about 60 minutes prior to the administration of the GM-CSF. In some embodiments, the other agent is an immune checkpoint inhibitor. In some embodiments, the vaccine composition described herein and another agent are administered simultaneously. In some embodiments, the vaccine composition described herein and another agent are administered sequentially. In some embodiments, the vaccine composition described herein and another agent are administered concurrently.

In some embodiments, the method for treating and/or preventing a labyrinthin-positive cancer in an individual comprises administering to the individual: (i) a vaccine composition, wherein the vaccine composition comprises an effective amount of an antigenic composition comprising: (a) a first peptide comprising SEQ ID NO:29 or a variant thereof, (b) a second peptide comprising SEQ ID NO:30 or a variant thereof; (c) a third peptide comprising SEQ ID NO:31 or a variant thereof; and (d) a fourth peptide comprising SEQ ID NO:32 or a variant thereof, and (ii) a composition comprising GM-CSF. In some embodiments, the vaccine composition is administered to the individual intradermally and the composition comprising GM-CSF is administered to the individual subcutaneously. In some embodiments, the vaccine composition and the composition comprising GM-CSF are administered to the individual within 60 minutes of one another. In some embodiments, each peptide comprises a T-cell epitope and a B-cell epitope. In some embodiments, the effective amount of an antigenic composition in a vaccine composition is between about 0.1 μg and about 1000 μg, such as about 75 μg and about 150 μg, such as about 100 μg. In some embodiments, the effective amount of an antigenic composition of a vaccine composition is between about 25 μg and about 75 μg. In some embodiments, the vaccine composition is LabVax 3(22)-23. In some embodiments, the method further comprises selecting the individual for the treatment based on a labyrinthin status of the cancer being indicative of a labyrinthin-positive cancer. In some embodiments, the labyrinthin status of the cancer is indicative of a labyrinthin-positive cancer when about 10% or greater of cancerous cells in a sample from the individual are positive for labyrinthin, such as determined using an immunohistochemical (IHC) technique. In some embodiments, the labyrinthin-positive cancer is an adenocarcinoma.

In some embodiments, the methods described herein for treating and/or preventing a labyrinthin-positive cancer in an individual comprises administering to the individual a vaccine composition described herein. In some embodiments, the method further comprises administering an adjuvant, such as GM-CSF. In some embodiments, the vaccine composition comprises one or more labyrinthin-derived peptides selected from the group comprising: (a) a first peptide comprising SEQ ID NO:25 or a variant thereof, (b) a second peptide comprising SEQ ID NO:26 or a variant thereof; (c) a third peptide comprising SEQ ID NO:27 or a variant thereof, and (d) a fourth peptide comprising SEQ ID NO:28 or a variant thereof. In some embodiments, the vaccine composition comprises: (a) a first peptide comprising SEQ ID NO:25 or a variant thereof; (b) a second peptide comprising SEQ ID NO:26 or a variant thereof; (c) a third peptide comprising SEQ ID NO:27 or a variant thereof; and (d) a fourth peptide comprising SEQ ID NO:28 or a variant thereof. In some embodiments, the vaccine composition comprises: (a) a first peptide comprising SEQ ID NO:25 or a variant thereof; (b) a second peptide comprising SEQ ID NO:26 or a variant thereof; (c) a third peptide comprising SEQ ID NO:27 or a variant thereof; and (d) a fourth peptide comprising SEQ ID NO:28 or a variant thereof, wherein these are the only four labyrinthin-derived peptides in the vaccine composition. In some embodiments, the labyrinthin-derived peptides are between 21 and 24 amino acids in length, such as 22 or 23 amino acids in length. In some embodiments, the vaccine composition comprising a peptide comprising SEQ ID NO:25 or a variant thereof comprises SEQ ID NO:29 or a variant thereof. In some embodiments, the vaccine composition comprising a peptide comprising SEQ ID NO:26 or a variant thereof comprises SEQ ID NO:30 or a variant thereof. In some embodiments, the vaccine composition comprising a peptide comprising SEQ ID NO:27 or a variant thereof comprises SEQ ID NO:31 or a variant thereof. In some embodiments, the vaccine composition comprising a peptide comprising SEQ ID NO:28 or a variant thereof comprises SEQ ID NO:32 or a variant thereof. In some embodiments, the vaccine composition comprises: (a) a first peptide comprising SEQ ID NO:29 or a variant thereof; (b) a second peptide comprising SEQ ID NO:30 or a variant thereof; (c) a third peptide comprising SEQ ID NO:31 or a variant thereof; and (d) a fourth peptide comprising SEQ ID NO:32 or a variant thereof, wherein these are the only four labyrinthin-derived peptides in the vaccine composition. In some embodiments, the labyrinthin-derived peptide comprises a T-cell epitope and/or a B-cell epitope. In some embodiments, the effective amount of an antigenic composition in a vaccine composition is between about 0.1 µg and about 1000 µg, such as about 75 µg and about 150 µg, such as about 100 µg. In some embodiments, the vaccine composition comprises GM-CSF. In some embodiments, the vaccine composition is LabVax 3(22)-23.

The methods disclosed herein are useful for treating or preventing a proliferative disease, such as a cancer, in an individual. In some embodiments, the cancer is a labyrinthin-expressing cancer. In some embodiments, the cancer is an adenocarcinoma.

In some embodiments, the cancer is an early stage cancer, a non-metastatic cancer, a primary cancer, an advanced cancer, a locally advanced cancer, a metastatic cancer, a cancer in remission, a recurrent cancer, a resistant cancer, or a refractory cancer. In some embodiments, the cancer is a localized resectable cancer (e.g., a tumor that is confined to a portion of an organ that allows for complete surgical removal), a localized unresectable cancer (e.g., a localized tumor that is unresectable because crucial blood vessel structures), or an unresectable cancer. In some embodiments, the cancer is, according to TNM classifications, a stage I tumor, a stage II tumor, a stage III tumor, a stage IV tumor, a N1 tumor, or a M1 tumor.

The methods disclosed herein are useful for treating or preventing a cancer, such as a labyrinthin-expressing cancer in an individual. In some embodiments, the individual has one or more of the following characteristics: (i) ability to understand and willingness to sign an informed consent form; (ii) at least 18 years of age with histologically confirmed adenocarcinoma and/or a labyrinthin-expressing cancer; (iii) previously treated with at least 1 prior systemic therapy (chemotherapy and/or biologic therapy) and either had no response/progressed during treatment or progressed following the completion of systemic therapy or refuses all other treatment; (iv) tumor(s) must overexpress the labyrinthin antigen, as determined by a screening immunohistochemical evaluation of the paraffin-embedded archival specimen demonstrating >10% of malignant cells staining for the antigen and with an intensity of at least 2× background according to the scoring by a single reference pathologist; (v) previous radiation therapy must have been completed at least 3 weeks prior to $1^{st}$ vaccine injection; (vi) any number of prior chemotherapy regimens; (vii) documentation of delayed type hypersensitivity (DTH) response to common recall antigens prior to $1^{st}$ vaccine injection; (viii) a performance status ≥60% on the Karnofsky scale; (ix) a life expectancy of ≥6 months at the time of 1st vaccine injection; (x) measurable or evaluable disease; (xi) a pretreatment absolute granulocyte count (AGC)≥1,000 and a pretreatment platelet count of ≥75,000 obtained within 4 weeks prior to $1^{st}$ vaccine injection; (xii) a pretreatment serum creatinine of ≤1.5 mg/dl is required. Measurements must be obtained within 4 weeks prior to 1st vaccine injection; and (xiii) a serum bilirubin≤1.5 and AST≤2.5× institutional upper limits of normal (≤5× if with liver metastases) obtained within 4 weeks prior to $1^{st}$ vaccine injection.

Methods of Producing Antibodies

The present disclosure, in some aspects, provides methods of producing an antibody in vivo, such as in a host animal. In some embodiments, the method comprises administering to a host animal an antigenic composition according to the disclosure herein. In some embodiments, the method comprises administering to a host animal a nucleic acid composition according to the disclosure herein. In some embodiments, the method comprises administering to a host animal a vaccine composition according to the disclosure herein.

Methods for producing antibodies in a host animal are known. See, e.g., Lee, B S et al., *Methods Mol Biol,* 1474, 2016, 25-47.

In some embodiments, the labyrinthin-derived peptide is conjugated to a carrier, such as a protein. In some embodiments, the labyrinthin-derived peptide is conjugated to an albumin, such as bovine serum albumin. In some embodiments, the labyrinthin-derived peptide is conjugated to keyhole limpet haemocyanin (KLH).

In some embodiments, the antibody is a polyclonal antibody. In some embodiments, the antibody is a monoclonal antibody.

In some embodiments, the method of producing an antibody further comprises purifying the antibody.

Those skilled in the art will recognize that several embodiments are possible within the scope and spirit of the disclosure of this application. The disclosure is illustrated further by the examples below, which are not to be construed as limiting the disclosure in scope or spirit to the specific procedures described therein.

EXAMPLES

Example 1

This example demonstrates the design, synthesis, and formulation of select labyrinthin-derived peptides according to the disclosure herein.

Peptides Designed for B-Cell and T-cell Immune Response

Labyrinthin-derived peptides were designed to produce B-cell and T-cell acquired immune system responses. Using the labyrinthin amino acid sequence (SEQ ID NO:1) as a starting template, 13 labyrinthin-derived peptides were designed, and four labyrinthin-derived peptide candidates were selected for further assessment and development (SEQ ID NO:29, SEQ ID NO:30, SEQ ID NO:31, and SEQ ID NO:32). The four selected labyrinthin-derived peptide candidates comprise amino acid sequences have known immunogenicity via the B-cell-mediated adaptive immune system and studies were conducted to confirm predicted binding to the MHCII complex groove to also trigger a T-cell-mediated adaptive immune system response.

The solubility of the four labyrinthin-derived peptide candidates was tested in silico for purposes of identifying peptide candidates suitable for formulation and administration. For example, the water solubility of labyrinthin-derived peptides candidates were tested using a Peptide property calculator (<http://www.pepcalc.com/>). All labyrinthin-derived peptide candidates were confirmed to have good water solubility.

Synthesis of Labyrinthin-Derived Peptides

The four labyrinthin-derived peptide candidates (SEQ ID NO:29, SEQ ID NO:30, SEQ ID NO:31, and SEQ ID NO:32) were synthesized. Each labyrinthin-derived peptide candidate sequence was confirmed using mass spectrometry. Specifically, an electrospray ionization mass spectrometry technique was used to obtain parent ion m/z spectra for each sample (a spectrum for SEQ ID NOS:29-32 is shown in FIGS. 1A-1D, respectively) followed by a tandem mass spectrometry technique to collect ion fragmentation data to confirm the peptide sequence of each labyrinthin-derived peptide candidate (data not shown).

The purity of each labyrinthin-derived peptide candidate was measured using a high-performance liquid chromatography technique measuring absorbance at 220 nm. The measured purity for each labyrinthin-derived peptide candidate is shown in Table 3.

TABLE 3

Purity of labyrinthin-derived peptides

| | Peptide purity (%) |
| --- | --- |
| SEQ ID NO: 29 | 96.289 |
| SEQ ID NO: 30 | 95.025 |
| SEQ ID NO: 31 | 95.019 |
| SEQ ID NO: 32 | 96.530 |

Solubility and Formulation of Labyrinthin-Derived Peptides

The solubility of each labyrinthin-derived peptide candidate was assessed by visual examination in ultrapure water, 0.1 M PBS (PBS; pH 7.4), and dimethyl sulfoxide (DMSO; analytical grade). As reported in Table 4, a solubility of less than 0.1 mg/mL of solvent was defined as "Undissolved" and solubility of greater than or 0.1 mg/mL was defined as "Dissolved." The concentration range of measured solubility is provided under the "Dissolved" classification where available (Table 4).

TABLE 4

Solubility of labyrinthin-derived peptides.

| | Ultrapure water | PBS (pH 7.4) | DMSO |
| --- | --- | --- | --- |
| SEQ ID NO: 29 | Dissolved ≤10 mg/mL | Dissolved ≤10 mg/mL | Dissolved N/A |
| SEQ ID NO: 30 | Undissolved | Dissolved ≤10 mg/mL | Dissolved ≤10 mg/mL |

TABLE 4-continued

Solubility of labyrinthin-derived peptides.

| | Ultrapure water | PBS (pH 7.4) | DMSO |
| --- | --- | --- | --- |
| SEQ ID NO: 31 | Undissolved | Undissolved | Dissolved ≤5 mg/mL |
| SEQ ID NO: 32 | Undissolved | Undissolved | Dissolved ≤10 mg/mL |

As observed, SEQ ID NO:30, SEQ ID NO:31, and SEQ ID NO:32 were undissolved in ultrapure water, which contradicts the predicted in silico solubility assessment described above. Formulation in a pH buffer (PBS, pH 7.4) did not improve solubility for SEQ ID NO:31 and SEQ ID NO:32.

Additional testing was completed to attempt to overcome the above-identified solubility issues. Results of the solubility tests performed for each labyrinthin-derived peptide candidate (SEQ ID NOS:29-32) are shown in Table 5. In short, all peptides were again dissolved in DMSO, confirming that the peptides had the capacity to dissolve in solution. Peptide solubility was then tested in normal saline (0.154 M sodium (NaCl)) and 0.2 M sodium (NaCl). Normal saline is generally an option as a solvent/diluent as use for such purpose is accepted by the Food and Drug Association. SEQ ID NO:31 and SEQ ID NO:32 did not dissolve in a normal saline solution. Additional solutions were tested to determine an alternative diluent to solubilize the candidate peptides, as determined by visual examination. As shown in Table 5, all four candidate peptides dissolved in 0.2 M saline solution.

TABLE 5

Solubility of labyrinthin-derived peptides.

| | SEQ ID NO: 29 | SEQ ID NO: 30 | SEQ ID NO: 31 | SEQ ID NO: 32 |
| --- | --- | --- | --- | --- |
| DMSO | Yes | Yes | Yes | Yes |
| 0.154M Sodium (NaCl) | Yes | Yes | No | No |
| 0.2M Sodium (NaCl) | Yes | Yes | Yes | Yes |

In further solubility testing, two tubes of 1.1 mg peptide for each of the four candidate peptides target was dissolved into 1 mL phosphate buffer (pH 10) (with and without 0.9% NaCl). After testing the solubility, the pH was serially adjusted with 2% acetic acid to lower the pH to the values shown in Table 6. The peptide solutions were subsequently stored at 4° C. for several hours to dissolve the peptides thoroughly. Following centrifugation, the peptide concentration that remained in solution was measured. The solubility (mg/mL) of each peptide candidate for each condition is listed in Table 6. The solubility of all four peptide candidates under all tested condition in Table 6 as above 0.3 mg/mL, and for each peptide candidate the variability of solubility across the pH ranges tested was minimal.

TABLE 6

| | | pH 10 mg/mL | pH 9 mg/mL | pH 8.5 mg/mL | pH 8 mg/mL | pH 7.5 mg/mL | pH 7 mg/mL | pH 6.5 mg/mL | pH 6 mg/mL | pH 5.5 mg/mL | pH 5 mg/mL | pH 4 mg/mL |
|---|---|---|---|---|---|---|---|---|---|---|---|---|
| | SEQ ID NO: | | | | | | | | | | | |
| PBS | 29 | 0.765 | 0.757 | 0.762 | 0.756 | 0.757 | 0.748 | 0.753 | 0.742 | 0.738 | 0.738 | 0.731 |
| without | 30 | 0.726 | 0.738 | 0.73 | 0.72 | 0.712 | 0.71 | 0.673 | 0.674 | 0.667 | 0.669 | 0.647 |
| NaCl | 31 | 0.849 | 0.857 | 0.854 | 0.847 | 0.812 | 0.825 | 0.769 | 0.773 | 0.819 | 0.802 | 0.777 |
| | 32 | 0.419 | 0.445 | 0.424 | 0.421 | 0.415 | 0.402 | 0.407 | 0.404 | 0.337 | 0.397 | 0.387 |
| PBS | 29 | 0.708 | 0.707 | 0.702 | 0.707 | 0.703 | 0.701 | 0.706 | 0.695 | 0.695 | 0.694 | 0.687 |
| with | 30 | 0.552 | 0.548 | 0.54 | 0.542 | 0.555 | 0.539 | 0.498 | 0.529 | 0.51 | 0.51 | 0.496 |
| 0.9% | 31 | 0.881 | 0.866 | 0.848 | 0.861 | 0.852 | 0.838 | 0.831 | 0.833 | 0.826 | 0.813 | 0.806 |
| NaCl | 32 | 0.413 | 0.426 | 0.433 | 0.415 | 0.412 | 0.412 | 0.406 | 0.411 | 0.412 | 0.401 | 0.382 |

Figure 2:
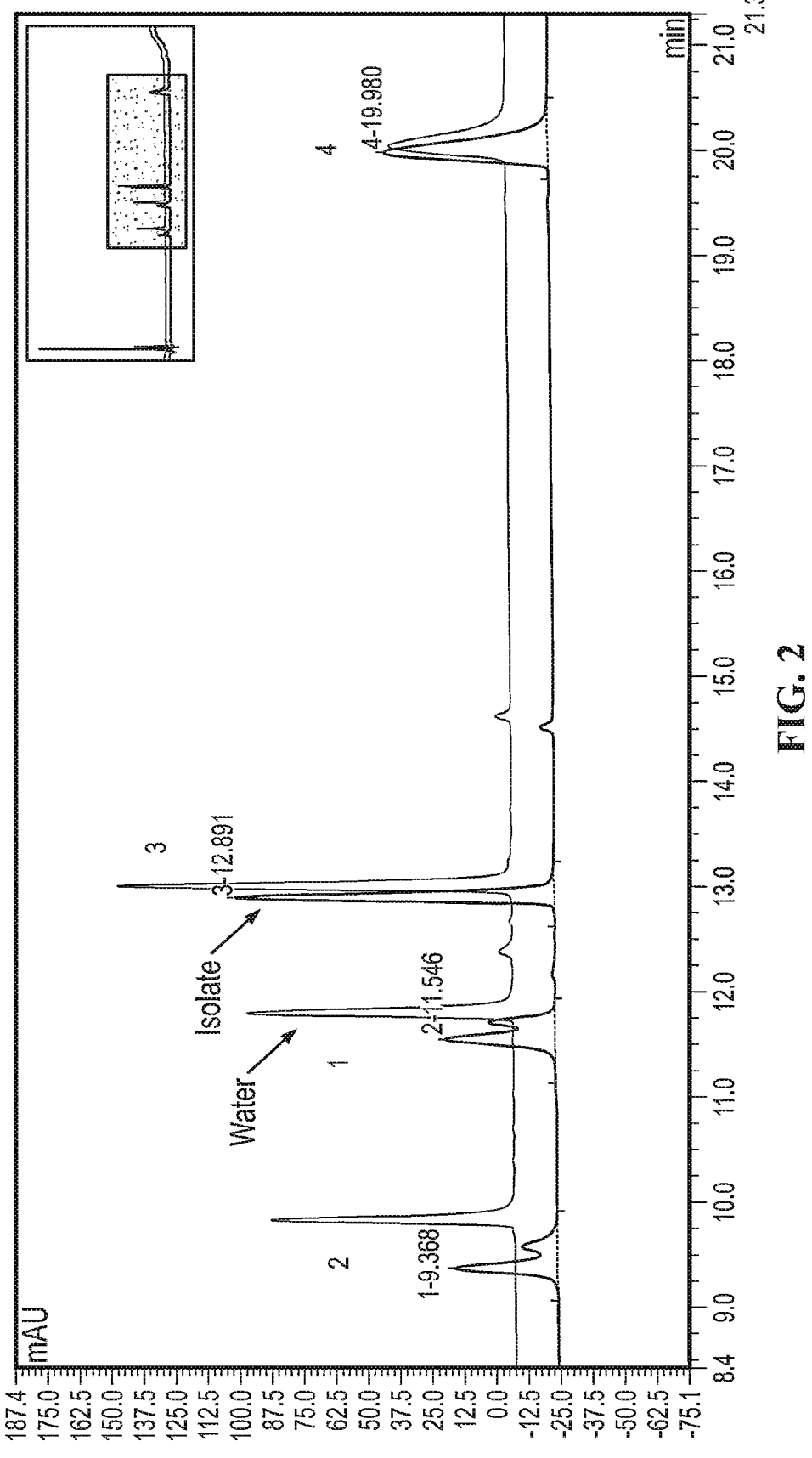
FIG. 2 shows UPLC tracings of four labyrinthin-derived peptides (SEQ ID NOS:29-32) reconstituted in isolyte (pH 7.4) or water.

A combination of each of the four peptides (SEQ ID NOS:29-32) were diluted in either water (pH of about 6.7-7) or isolyte (pH 7.4) and analyzed by an ultra-performance liquid chromatographic (UPLC) technique develop to analyze the peptides in a solution for a vaccination. As illustrated in FIG. 2, numbers 1-4 correspond in order with the peptides of SEQ ID NOS:29-32.

Each peptide has a very low pI and the results illustrated in FIG. 2 show that buffering to a physiologic level led to the detection of doublets in all four peptides. The doublets were especially pronounced for peptides #1 (SEQ ID NO:29) and #2 (SEQ ID NO:30). As designed for each peptide, when the peptides reconstituted in isolyte were diluted further with water the UPLC tracing for each peptide resolved into a single peak (data not provided), such as observed for the peptides reconstituted in water in FIG. 2. This data indicates that (1) the peptides became charged as they are in an environment several pH units above their acidic pI's, and (2) the peptide structure remains intact as evidenced by each peptide resolving into a single peak and returning to the original retention times upon serial dilution with water (returning to a more acidic pH).

Example 2

The example demonstrates the inhibition of tumor growth by a vaccine containing four labyrinthin-derived peptides (SEQ ID NOS:29-32) (LabVax 3(22)-23).

C57BL/6 hPD-1/PD-L1 mice subcutaneously implanted with MC 38 murine colon (adenocarcinoma) tumor cells were administered either: (a) 40 μg of LabVax (10 μg of each peptide, i.d.) in combination with mouse GM-CSF (1 μg, s.c.) as an adjuvant; or (b) saline control, on days 15, 26, and 40 after tumor implantation. Body weight and tumor weight were measured during the study. Statistical analyses of the mouse weight and tumor weight are provided in Table 7.

Figure 3:
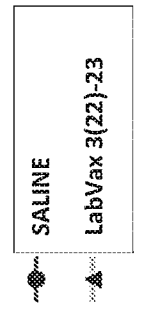
FIG. 3 shows a graph of tumor weight (mg) versus days following administration of a peptide vaccine (LabVax 3(22)-23) or a saline control to mice subcutaneously implanted with MC 38 murine colon (adenocarcinoma) tumor cells.
Figure 3:
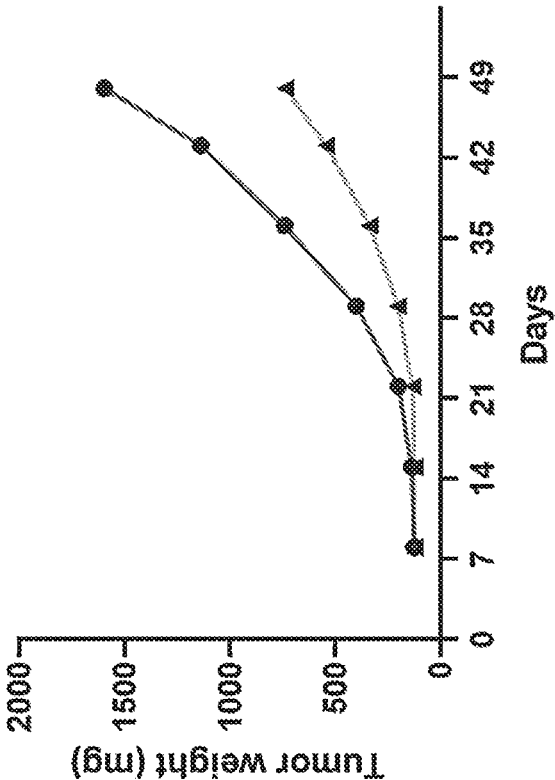

Body weights during the course of study were not different between the vaccine versus saline control administration groups and no adverse events were noted in either group. The results show that the vaccine produced a significant decrease in tumor growth (FIG. 3), and thus LabVax 3(22)-23 has antitumor activity without toxicity in immune competent mice.

The results with respect to safety are in agreement with formal studies performed under Good Laboratory Practices in Balb/C mice (Comparative Biosciences, Inc.; Sunnyvale, CA) which showed no toxicity by the individual peptides, nor the combination [LabVax 3(22)-23] after 5 injections (50 μg each peptide) over a 49 day period.

Additionally, studies in mice that have seroconverted are in agreement with the finding that the use of the peptides is safe. Preclinical acute (2 injections over 14 days) and long term (4 injections over 49 days) testing of LabVax 3(22)-23 in mice were performed under an approved GLP animal study. The dosage was approximately the equivalent of ~120× the intended human dosage (400 μg per injection). No clinically observed adverse events or abnormalities have been noted throughout four injections.

Example 3

To test for the production of antibodies after administration of peptides described herein, 12 Balb/c mice were split into 4 treatment groups with each treatment group assigned to receive an injection of one of SEQ ID NO: 29-32. As shown in the Table 8, positive clones were identified in each treatment group.

TABLE 8

| Number of positive clones identified for each treatment group | |
|---|---|
| PEPTIDE SEQ ID NO. | Positive clones/hybridomas |
| 29 | 3 |
| 31 | 8 |

TABLE 7

| Statistical analyses of mouse weight and tumor weight. | | | | | |
|---|---|---|---|---|---|
| | Tukey's multiple comparisons test | Mean Diff. | 95.00% CI | Significant? | Adjusted P value |
| MOUSE WEIGHT (mice bearing tumors—tumor) | Saline vs. LabVax | 0.5757 | −0.07956 to 1.231 | NS | 0.1143 |
| TUMOR WEIGHT | Saline vs. LabVax | 305.5 | 179.8-431.1 | YES | <0.0001 |

TABLE 8-continued

Number of positive clones identified for each treatment group

| PEPTIDE SEQ ID NO. | Positive clones/hybridomas |
| --- | --- |
| 31 | 10 |
| 32 | 3 |

Example 4

This example demonstrates a Phase I study of a four-peptide labyrinthin cancer vaccine (LabVax 3(22)-23) in patients with adenocarcinomas. The four peptides of the vaccine are SEQ ID NOs:29-32.

Patients (12) selected for the Phase I study have inoperable or metastatic solid tumors (adenocarcinomas) who failed standard of care treatment. Two treatment cohorts will be established based on the following: Cohort A: 6 patients administered (i.d.) LabVax 3(22)-23 alone; and Cohort B: 6 patients administered (i.d.) LabVax 3(22)-23 +GM-CSF (adjuvant). Phase I expansion, should it occur, will include the following: 7 patients with breast adenocarcinoma; 7 patients with lung adenocarcinoma; 10 patients with other adenocarcinomas that are labyrinthin-positive. Adenocarcinomas, all MCA 44-3A6 positive (mouse monoclonal anti-labyrinthin antibody), will be included in each of the cohorts in the expanded trial segment.

The primary objective of this study is to demonstrate that the synthetic four-peptide cancer vaccine causes no short-term adverse effects in humans.

The secondary objectives of this study are to: (i) compare safety of the vaccine with/without GM-CSF (adjuvant); (ii) obtain preliminary assessment on the efficacy of the vaccine with/without GM-CSF (adjuvant); (iii) compare safety of the vaccine (with or without GM-CSF) in more specific areas of labyrinthin-positive breast and lung patients, as well as a cohort of other adenocarcinomas that are labyrinthin-positive; and (iv) obtain preliminary assessment of the vaccine (with or without GM-CSF) in more specific areas of labyrinthin-positive breast and lung patients, as well as a cohort of other adenocarcinomas that are labyrinthin-positive.

Formulation, bottling, QA, QC, sterility testing, and labeling is scheduled to be performed under cGMP. Further QA/QC stability testing is scheduled to be performed at Emery Pharma. Peptides will be reconstituted in Isolyte S pH 7.4 to a concentration of 400 μg/100 μl (containing 100 μg each of the four peptides), sterile filtered. The final product has a pH of about 6.5-7. The vaccine will then be aliquoted into vials for clinical use then stored at −80° C. Ongoing studies have demonstrated that the peptides can be made in this manner and reconstituted without any effect on the structural integrity of the peptides (per GLP certified UPLC analysis; Emery Pharma, Alameda, CA).

For example, a computer-based analysis of the four peptides was conducted by SafeBridge Consultants, Inc. (New York, NY and Mountain View, CA), and achieved an Occupational Health Categorization: Category 2 of 4. The score indicates that the peptides were safe and were only marginalized in their score due to lack of available data in the literature For Cohort B, 100 mcg human GM-CSF will be administered subcutaneously 45-60 minutes prior to the LabVax 3(22)-23 (i.d.) injection. GM-CSF is to be injected within 3 cm of the vaccine injection site, using a 28 gauge needle.

Subjects with advanced/metastatic or recurrent adenocarcinoma (stage IV) of any primary site, with emphasis on breast and non-small cell lung cancer that is incurable with available therapies will be recruited from the UC Davis Comprehensive Cancer Center for Cohort A and Cohort B. The follow-up Phase I expansion will be opened to earlier stage adenocarcinoma subjects with labyrinthin-positive tumors.

Patients must meet all of the following criteria to be eligible for study entry: (i) ability to understand and willingness to sign an informed consent form; (ii) patients of at least 18 years of age with histologically confirmed adenocarcinoma; (iii) patients must have been previously treated with at least 1 prior systemic therapy (chemotherapy and/or biologic therapy) and either had no response/progressed during treatment or progressed following the completion of systemic therapy or refuses all other treatment; (iv) tumors must overexpress the labyrinthin antigen, as determined by a screening immunohistochemical evaluation of the paraffin-embedded archival specimen demonstrating >10% of malignant cells staining for the antigen and with an intensity of at least 2× background according to the scoring by a single reference pathologist; (v) previous radiation therapy must have been completed at least 3 weeks prior to $1^{st}$ vaccine injection. There must be no plans for the patient to receive concurrent radiation therapy to measurable lesions. The measurable lesion may be in the field(s) of prior radiation provided that the lesion is demonstrated by CT scan to be progressing or stable; (vi) any number of prior chemotherapy regimens is allowed. Prior chemotherapy must have been completed at least 3 weeks prior to 1st vaccine injection and patients must have recovered from all toxicities of the prior treatment before $1^{st}$ vaccine injection; (vii) patients must have documentation of delayed type hypersensitivity (DTH) response to common recall antigens prior to 1st vaccine injection. As part of the prescreen evaluation, patients will undergo DTH testing to at least one common recall antigen; selection will be at the discretion of the physician, based upon the history and physical (mumps, Trichophyton, Candida antigens, flu matrix, and/or PPD, etc.). Skin tests will be read at or about 48 hours. A skin reaction will be considered positive if there is any measurable induration associated with erythema of 10 mm or greater. Erythema alone will not be regarded as a positive DTH response; (viii) all patients must have a performance status ≥60% on the Karnofsky scale; (ix) all patients must have a life expectancy of ≥6 months at the time of 1st vaccine injection; (x) all lab work and all radiologic tests (e.g., x-rays, CT) must be done within 4 weeks prior to $1^{st}$ vaccine injection; (xi) patients must have measurable or evaluable disease (see section 10). All patients must have a pretreatment absolute granulocyte count (AGC)≥1,000 and a pretreatment platelet count of ≥75,000 obtained within 4 weeks prior to $1^{st}$ vaccine injection; (xii) a pretreatment serum creatinine of ≤1.5 mg/dl is required. Measurements must be obtained within 4 weeks prior to 1st vaccine injection; (xiii) patients must have a serum bilirubin≤1.5 and AST≤2.5×institutional upper limits of normal (≤5× if with liver metastases) obtained within 4 weeks prior to $1^{st}$ vaccine injection; (xiv) because of their relatively short life expectancy which will preclude assessment of this vaccine's activity and toxicity, patients with known brain and/or leptomeningeal metastases are excluded; and (xv) because the effects of the vaccine on the unborn fetus or nursing infant are unknown, pregnant and nursing women are ineligible. Women of child bearing age must have a negative urine or serum pregnancy test (HCG).

Patients who meet any of the following criteria will be excluded from study entry: (i) known active immunological disease, autoimmune disease, hereditary or congenital immunodeficiencies, underlying immunodeficiency, or altered immune function (e.g., active Grave's disease, AIDS/ HIV, Addison's disease, myasthenia gravis, severe atopic dermatitis, rheumatoid arthritis, eczema scleroderma, Goodpasture's syndrome, Sjogren's syndrome, ankylosing spondylitis, Hashimoto's thyroiditis, systemic lupus erythematosus, autoimmune neutropenia/thrombocytopenia, immune-mediated hemolytic anemia, or previous history of anaphylaxis requiring ICU care). Contact the Principal Investigator for any clarifications regarding this criterion; (ii) patients who have had a prior splenectomy are ineligible because of a compromised immune function; (iii) pregnant or lactating women; (iv) any medical condition including additional malignancies, laboratory abnormalities, or psychiatric illness that would prevent the subject from participating and adhering to study related procedures; (v) uncontrolled concomitant disease that in the opinion of the investigator would interfere with the patient's safety or compliance on trial; and (vi) severe infection that in the opinion of the investigator would interfere with patient safety or compliance on trial within 4 weeks prior to enrollment.

Dose limiting toxicity (DLT) in a given patient is defined as any grade III non-hematologic toxicity not reversible to grade II or less within 96 hours, or any grade IV toxicity. DLT is based on the first course of treatment. Toxicity will be graded according to the NCI Common Terminology Criteria for Adverse Events (CTCAE; version 5.0). To be evaluable for toxicity, a patient must receive at least 1 complete course of treatment and be observed for at least 6 months after the start of the first course or have experienced DLT. All patients who are not evaluable for toxicity will be replaced.

Maximum tolerated dose (MTD) is defined as the highest amount of injections tested in which fewer than 33% of patients experienced DLT attributable to the study drugs (LabVax 3(22)–23±adjuvant), when at least 6 patients were treated at that dose and are evaluable for toxicity. The MTD is 1 injection level below the lowest dose tested in which 33% or more patients experienced DLT attributable to the study drugs. At least 6 patients will be treated at the MTD.

The DLT-level is the lowest injection level tested in which 33% or more patients experienced DLT attributable to the study drug(s); the DLT-level is 1 dose level above the MTD.

Six patients for each vaccine/vaccine+GM-CSF group will be treated at the scheduled intervals up to 5 through 12 weeks. If 0/3 of the first patients in each group experience DLT after the first 2 injections, the next 3 patients will be enrolled while the initial group continues with the injection schedule. If DLT attributable to the study drug(s) is experienced in exactly 1/3 patients, 3 more patients (for a total of 6) will be treated up to that injection series amount. If no additional DLT is observed at the expanded injection schedule (i.e., no more than 1/6 with DLT), the injection regimen will continue. Injections terminate as soon as 2 or more patients experience any DLT attributable to the study drug(s), at a given injection frequency. The Phase I trial will be closed when 6 patients for each group have been treated and at most 1/6 patients experience DLT. If more than 1/6 patients experience DLT, the next lower amount of injections will be used in the remaining patients.

All patients who have not experienced any DLT at the intervals (just prior to) will continue with the next injection as necessary. Treatment will continue in an individual patient according to the injection schedule if no DLT is observed and if benefit is observed; patients will go off therapy for unacceptable toxicity (as determined by the treating physician and/or the patient), or toxicity requiring discontinuation of treatment.

Based on the first-into-human clinical trial, after the patients complete the 12-week injection schedule, and 1-month follow-up phase, the patients that have stable or tumor regression will be offered, off study, additional vaccinations (e.g., boosters, patient seroconversion initiating). The treating physician will determine the injection frequency.

All patients being considered for this trial will be pre-screened prior to protocol therapy to determine that tumors overexpress the labyrinthin antigen, as determined by a screening immuno-histochemical evaluation of the paraffin-embedded archival specimen demonstrating >10% of malignant cells staining for the antigen. A single reference pathologist will make this assessment.

This is a single site, open-label trial of the synthetic peptide cancer vaccine LabVax 3(22)-23 directed at producing an immune response to the tumor-associated antigen. The design of the study will be to examine safety of the vaccine (±GM-CSF as adjuvant) in a pilot group of adenocarcinoma patients. Preliminary information will be obtained regarding efficacy and post study correlates about seroconversion will be made.

Vials will be supplied containing enough peptide vaccine to achieve in injection of 400 μg/100 μl (100 μg for each of the four peptides) diluted in Isolyte S pH 7.4. GM-CSF (250 μg/vial) will be used in accordance with the manufacturer's information. A concomitant administration of 100 μg is to be administered with each LabVax 3(22)-23 injection.

Patients will be given 400 μg peptide vaccine contained in a total volume of 0.1 ml intradermally on weeks 1, 2, 4, 8, and 12 (additional vaccinations on weeks 24 and 36 pending clinical responsivity). The vaccine will be stored at –20° C. and warmed to room temperature prior to use. The vaccine should be used within one hour of reaching room temperature.

A 1 ml syringe with a 28-gauge needle or smaller is to be used to draw up 0.1 ml from a single vial. The total volume will be injected intradermally after 60% (about 4 mm) of the needle length has been threaded into the dermis.

After the fluid has been injected, the needle/syringe is to be held in place for 5 minutes (may be taped in place), in order to prevent back flow. Any bandage over the injection site is to be placed such that pressure is not exerted on the injected fluid. Patients are to be advised to avoid applying pressure to the injection site until the fluid is absorbed. Sterile saline will be used to reconstitute to achieve an equivalent co-administration of 100 μg of GM-CSF (when used) and administered within one hour of vaccination. Alternative injection sites, as appropriate, will be located in either leg or abdomen. It is the intent to give each of the series of vaccinations at slightly different sites (3 cm from the last injection site if the previous injection site can be seen), and the relative locations will be recorded. Any inflammation of the site will be documented (photographed and/or written record). Inflammation is defined as an area of persistent redness and/or induration greater than 20 mm surrounding the injection site lasting greater than 1 week or any skin ulceration.

The first 3 patients from each group (±GM-CSF) will be observed for 60 minutes post immunization for the first 5 immunizations. Temperatures, vital signs, and reactions will be assessed by the staff at the end of the post immunization period every fifteen minutes. Patients will take and record their temperatures the same evening (and at additional times if they have symptoms of fever) and record any other symptoms they experience. If patients report any skin changes, they will be asked to come in for evaluation. Provided that there are no serious adverse effects noted in the first 6 patients through their first 5 doses, the monitoring time will be waived for the remainder of their injections. Patients 7-12 will be monitored for 60 minutes immediately following their first vaccine injection; subsequent injections will not require post-vaccine observation unless clinically indicated.

Serum samples will be collected on weeks 0, 1, 2, 4, 8, 12, and 14 (or within 10-20 days after the last injection, including if additional vaccine injections are, to assess seroconversion post trial, but will also be available to ascertain any systemic toxicity, if warranted. Serum samples will be collected just prior to each vaccination.

A maximum of 3 patients will be enrolled each week until the first 6 patients have received 5 doses with no adverse events (Grade >2).

If intradermal injection results in skin ulcerations, subsequent injections can be given subcutaneously for the remaining vaccinations. As vaccinations are being administered intradermally (i.d.), if a patient developed a significant immune response, the DTH reaction would preclude further intradermal administration. A significant DTH response is defined as persistent redness and induration greater than 20 mm surrounding the injection site lasting greater than 1 week or any skin ulceration.

Subjects will be evaluated for 31 weeks to include a follow-up exam 4 weeks after the last-injection (or last injection if injections are stopped earlier). Thereafter they will be evaluated for immunologic parameters on the 4th and 7th month after the last injection.

Patients may receive ongoing supportive and palliative care (e.g., nutritional support, pain control) as clinically indicated throughout the study. Patients may not be receiving any concurrent oncologic or cancer-directed therapy (e.g., chemotherapy, biologic therapy, etc.). Bisphosphonate therapy is allowed as part of supportive care. Patients who develop urgent complications in previously documented sites of disease may receive palliative radiation therapy. Continuation on the protocol therapy will be determined by discussions with the sponsor and the investigator, if medically appropriate.

A patient will be removed from protocol treatment if any of the following conditions are satisfied: (i) unacceptable toxicity (as determined by the treating physician and/or the patient), or toxicity requiring discontinuation of treatment; (ii) patients may choose to withdraw from the study at any time for any reason; (iii) patients may be withdrawn from the protocol at the investigator's discretion if the investigator feels that continuation is not in the patient's best medical interest or if the patient is non-compliant with treatment; (iv) progression of disease characterized by the development of new lesions or if existing disease increases by over 100% of the baseline or nadir (whichever is smaller) long-axis unidimensional diameter; (v) progression of disease per RECIST (Response Evaluation Criteria in Solid Tumors) criteria; and (vi) completion of protocol therapy as follows: (a) completion of 5 planned vaccinations; and (b) final dose of 12th patient (Phase I) or 30th patient (Phase I expanded segment). Patients that start, but do not complete the full injection schedule for a given cohort are not counted towards the patient totals required to complete each respective cohort; their data will be included in the study summary.

If patients fail to respond to the protocol treatment and/or are removed from the therapy because of toxic effects or "disease progression", further treatment, if any, is at the discretion of the investigator.

After removal from protocol treatment, all patients will be followed for late toxicities. Patients will be seen 4 weeks, 12 weeks and 28 weeks after coming off therapy (last injection). If ongoing toxicities have not resolved to ≤grade 1 within the first 4 weeks, patients are to be seen every month until toxicity resolves to ≤grade 1. No new toxicities after the 4-week follow-up will be reported unless considered related to protocol treatment by the investigator. Final report form will be required on all patients either after the final follow-up or at the time of death.

Patients will be enrolled on the study as outlined above. If, at any time during the study, there is sufficient evidence suggesting an excessive Grade 3 or Grade 4 toxicity rate, the study will be terminated. An excessive Grade 3 toxicity rate will be taken to be 20% (or 4 patients) and an excessive Grade 4 toxicity rate will be taken to be 10% (or 2 patients) of the patients enrolled to that date. Evidence that the toxicity rate is excessive will be considered sufficient if the lower limit of the 90% one-sided confidence interval for the estimate of the toxicity rate exceeds the appropriate limit (20% for Grade 3, 10% for Grade 4).

Operationally, this will occur if any of the following occur: (i) grade 3 Toxicity (n=20): 2 of the first 2 patients, 3 of the first 6 patients, 4 of the first 9 patients, 5 of the first 13 patients, 6 of the first 14 patients, or 7 of the first 19 patients; or(ii) grade 4 Toxicity (n=20): 2 of the first 5 patients, 3 of the first 11 patients, 4 of the first 18 patients, or 5 of the first 19.

The toxicity scale, definitions, and specific criteria for each toxicity level will be those as outlined in the guidelines defined by the CTCAE version 3.0. If the patient develops any grade 3 or greater hematologic or non-hematologic toxicity that is possibly, probably, or definitely related to the immunizations, no further vaccinations will be given to that patient and the patient will be removed from protocol therapy. There will be no vaccine dose modifications allowed. If the Grade ≥3 toxicity observed is determined by the investigator to be related to the immune response generated, a regimen of corticosteroids.

A comprehensive metabolic panel will be performed on serum (including total bilirubin, SGOT, and creatinine), and monitored on weeks 0, 1, 2, 4, 8, and 12; and on any additional vaccination weeks if deemed necessary according to the schema (i.e., weeks 24 and 36). In addition, the patient will undergo a physical examination at the first immunization and then at each vaccination. Patients will be observed for the development of autoimmunity in normal tissues which may express basal levels of labyrinthin, especially in the skin and salivary glands.

Baseline evaluations are to be conducted within 14 days prior to $1^{st}$ vaccine injection unless otherwise noted. Scans and X-rays must be performed within 28 days prior to $1^{st}$ vaccine injection. In the event that the patient's condition is deteriorating, laboratory evaluations should be repeated within 48 hours prior to initiation of the next cycle of therapy.

TABLE 9

Study schedule.

| Week or Event | Pre-Study[a] | 1 | 2 | 4 | 8 | 12 | 16[b] | Off Study[c] |
|---|---|---|---|---|---|---|---|---|
| LabVax 3(22)-23 [d] | | X | X | X | X | X | | |
| Informed Consent | X | | | | | | | |
| Demographics | X | | | | | | | |
| Medical History | X | | | | | | | |
| Physical Exam[e] | X | X | X | X | X | X | X | |
| Performance Status[f] | X | X | X | X | X | X | X | |
| IHC on Tumor Tissue | X | | | | | | X | |
| Serum for Antibody Titer | X | X | | X | | X | | X |
| CBC | X | X | | X | | X | X | |
| Chemistry | X | X | | X | | X | X | |
| DTH[c] | X | | | | | | X | |
| Pregnancy Test[a] | X | | | | | | | |
| Tumor Evaluation[e] | X | | | | | X | | |

[a]Pre-study requirements (within 4 weeks prior to 1st vaccine injection except where otherwise indicated); DTH, pregnancy test, biopsy for immunohistochemistry included in pre-study exam.
[b]First of 3 follow-ups as defined in section 7.4.8. Booster vaccinations may be administered at the discretion of the physician and patient, provided material is available.
[c]It is preferable that 2 consecutive measurements taken 4 weeks apart be used to document progressive disease if the patient is removed from study for this reason.
[d] LabVax 3(22)-23 (0.1 ml, id.) ± GM-CSF.
[e]Routine to include vital signs, height (pre-study only needed), weight.
[f]Tumor evaluation (clinical measurements; as indicated: radiographic scans, biopsy for immunohistochemistry, etc).
g. Comprehensive metabolic panel (including serum creatinine, AST, total bilirubin; CBC w/auto differential for pre-study at a minimal).

Within 4 weeks prior to $1^{st}$ vaccine injection except where otherwise indicated: (i) History and Physical Exam including: Height, Weight, Performance status, Clinical tumor measurements; (ii) hematology: Complete blood count with auto differential; (iii) biochemistry: Serum creatinine, AST, total bilirubin; and (iv) radiology: Scans/X-rays as necessary to document disease (within 3 months prior to 1st vaccine injection). To ensure comparability, the baseline X-rays/scans and subsequent X-rays/scans to assess response must be performed using identical techniques; i.e. scans performed immediately following bolus contrast administration using a standard volume of contrast, the identical contrast agent, and preferably the same scanner.

Other investigations will include: (i) baseline Serum Sample (for antibody titers); (ii) pregnancy test (for women of childbearing potential) within 2 weeks prior to 1st vaccine injection; (iii) DTH to common recall antigens within 3 months prior to 1st vaccine injection; and (iv) immunohistochemistry (tumor tissue must be positive for labyrinthin expression for eligibility) should be performed within 3 months prior to 1st vaccine injection.

All patients will be evaluable for toxicity from the time of their first treatment with LabVax 3(22)-23. All patients will be evaluable for toxicity from the peptide injections and will be monitored for acute toxicity. All patients will be monitored for 1 hour post injection for the first 3 injections with a physician within immediate proximity.

Response and progression will be evaluated in this study using the new international criteria proposed by RECIST (Response Evaluation Criteria in Solid Tumors) committee. Changes in only the largest diameter (unidimensional measurement) of the tumor lesions are used in the RECIST criteria.

Measurable lesions are defined as those that can be accurately measured in at least one dimension (longest diameter to be recorded) as ≥20 mm with conventional techniques (PE, CT, XR, MRI) or as ≥10 mm with spiral CT scan. All tumor measurements must be recorded in millimeters (or decimal fractions of centimeters).

All other lesions (or sites of disease), including small lesions (longest diameter <20 mm with conventional techniques or <10 mm with spiral CT scan) are considered non-measurable disease. Bone lesion, leptomeningeal disease, ascites, pleural/pericardial effusions, lymphangitis cutis/pulmonis, inflammatory beast disease, abdominal masses (not followed by CT or MRI) and cystic lesions are all non-measurable. Prostate cancer patients may also have PSA-only disease.

All measurable lesions up to a maximum of 5 lesions per organ and 10 lesions in total representative of all involved organs should be identified as target lesions and be recorded and measured at baseline. Target lesions should be selected on the basis of their size (lesions with the longest diameter) and their suitability for accurate repetitive measurements (either by imaging techniques or clinically). A sum of the longest diameter (LD) for all target lesions will be calculated and reported as the baseline sum LD. The baseline sum LD will be used as reference to further characterize the objective tumor response of the measurable dimension of the disease. If there are >10 measurable lesions, those not selected as target lesions will be considered together with non-measurable disease as non-target lesions.

All non-measurable lesions (or sites of disease) plus any measurable lesions over and above the 10 listed as target lesions. Measurements are not required but these lesions should be noted at baseline and should be followed as "present" or "absent".

All patients will have their best response on study classified as outlined below: Complete Response (CR): disappearance of all clinical and radiological evidence of tumor (both target and non-target); Partial Response (PR): at least a 30% decrease in the sum of LD of target lesions taking as reference the baseline sum LD; and stable Disease (SD): steady state disease. Neither sufficient shrinkage to qualify for PR nor sufficient increase to qualify for PD; Progressive Disease (PD): at least a 20% increase in the sum of LD of measured lesions taking as references the smallest LD recorded since the treatment started or the appearance of one or more new lesions. Appearance of new lesions will also constitute progressive disease. In exceptional circumstances unequivocal progression of non-target lesions may be accepted as evidence of disease progression. In exceptional circumstances unequivocal progression of non-target lesions may be accepted as evidence of disease progression.

TABLE 10

Response classifications.

| Target Lesions | Non-Target Lesions | New Lesions | Overall Response | Best Response For This Category Also Requires |
|---|---|---|---|---|
| CR | CR | No | CR | ≥4 weeks confirmation |
| CR | Non-CR/Non-PD | No | PR | ≥4 weeks confirmation |
| PR | Non-PD | No | PR | ≥4 weeks confirmation |
| SD | Non-PD | No | SD | Documented at least ≥ 4 weeks from baseline; ≥8 weeks for PSA-only disease |
| PD | Any | Yes or No | PD | No prior SD, PR, or CR |
| Any | PD | Yes or No | PD | No prior SD, PR, or CR |
| Any | Any | Yes | PD | No prior SD, PR, or CR |

Response duration will be measured from the time measurement criteria for CR/PR (whichever is first recorded) are first met until the first date that recurrent or progressive disease is objectively documented. Stable disease duration will be measured from the time of start of therapy until the criteria for progression are met, taking as reference the smallest measurements recorded since the treatment started.

Clinical serological studies will be performed in all patients after the course of this study to assess any development of serum antibodies directed against the labyrinthin-based peptides. The antibody response will be measured and evaluated as the total immunoglobulin (IgM, IgG, IgA, IgD, and IgE) response to the labyrinthin-based peptides (all 4 combined). Individual IgM and IgG responses will be measured for research purposes and will not be used in this study to direct treatment. IgG subclass responses will also be determined for research purposes and will not be used to direct treatment. These responses will be evaluated at weeks 4, 9, 12, 15, 19, 23, and 27.

A blood sample of 10 ml is to be drawn as outlined above. Each sample will be collected into a non-heparinized vacutainer with a 20 g or larger needle. Blood samples will be cooled immediately on wet ice (approximately 4-8 C) and kept at this temperature until processed to separate the serum. The serum will be spiked with sodium azide as preservative (final concentration greater within 0.05-0.1% using a saturated sodium azide solution) with the volume of addition recorded along with the total amount of serum. The samples should be divided equally and stored at −80° C. in two different freezers until analyses.

The serum should never be frozen. Samples (10 cc) should be kept in the refrigerator (4° C.) in their collecting tubes (provided by LabyRx, Inc.; sodium azide, non-heparinized red top tubes with wax phase separator). Serum samples will remain at the institution and shipped in bulk later during the trial. The reserve of serum is to safeguard against the loss of a sample in shipment or at the subsequent storage site.

Patients who seroconvert to 1:100,000 will be requested (optional; one time only) to provide 10 ml of whole blood for the isolation of viable lymphocyte cells. The whole blood will be processed on a Ficoll step gradient, the cells washed 3 times with Hanks Buffer, and the cells aliquoted and cyropreserved (about $5 \times 10^6$/vial) in 10% DMSO/90% Fetal Calf Serum. These cells will be given to LabyRx (or a third-party testing laboratory) for the evaluation of cellular immune responses and other research related studies.

Prior to patient treatment, a formalin fixed paraffin embedded tissue with a representative sample of tumor tissue must be submitted for immunohistochemical staining and detection/evaluation of labyrinthin.

---

What is claimed is:

1. A method for treating a labyrinthin-positive adenocarcinoma in an individual in need thereof, the method comprising administering to the individual having the labyrinthin-positive adenocarcinoma a vaccine composition comprising:

(a) an effective amount of an antigenic composition comprising:

(i) a first peptide consisting of SEQ ID NO:29;

(ii) a second peptide consisting of SEQ ID NO:30;

(iii) a third peptide consisting of SEQ ID NO:31; and (iv) a fourth peptide consisting of SEQ ID NO:32; and (b) a pharmaceutically acceptable vehicle.

* * * * *

```
                          SEQUENCE LISTING

<160> NUMBER OF SEQ ID NOS: 32

<210> SEQ ID NO 1
<211> LENGTH: 255
<212> TYPE: PRT
<213> ORGANISM: Homo sapiens

<400> SEQUENCE: 1

Met Val Ile Ala Leu Leu Gly Val Trp Thr Ser Val Ala Val Val Trp
1               5                   10                  15

Phe Asp Leu Val Asp Tyr Glu Glu Val Leu Gly Lys Leu Gly Ile Tyr
                20                  25                  30

Asp Ala Asp Gly Asp Gly Asp Phe Asp Val Asp Asp Ala Lys Val Leu
            35                  40                  45

Leu Gly Leu Lys Glu Arg Ser Thr Ser Glu Pro Ala Val Pro Pro Glu
    50                  55                  60

Glu Ala Glu Pro His Thr Glu Pro Glu Glu Gln Val Pro Val Glu Ala
65                  70                  75                  80

Glu Pro Gln Asn Ile Glu Asp Glu Ala Lys Glu Gln Ile Gln Ser Leu
                85                  90                  95

Leu His Glu Met Val His Ala Glu His Val Glu Gly Glu Asp Leu Gln
            100                 105                 110

Gln Glu Asp Gly Pro Thr Gly Glu Pro Gln Gln Glu Asp Asp Glu Phe
            115                 120                 125

Leu Met Ala Thr Asp Val Asp Asp Arg Phe Glu Thr Leu Glu Pro Glu
    130                 135                 140

Val Ser His Glu Glu Thr Glu His Ser Tyr His Val Glu Glu Thr Val
145                 150                 155                 160

Ser Gln Asp Cys Asn Gln Asp Met Glu Glu Met Met Ser Glu Gln Glu
                165                 170                 175

Asn Pro Asp Ser Ser Glu Pro Val Val Glu Asp Glu Arg Leu His His
            180                 185                 190

Asp Thr Asp Asp Val Thr Tyr Gln Val Tyr Glu Glu Gln Ala Val Tyr
            195                 200                 205

Glu Pro Leu Glu Asn Glu Gly Ile Glu Ile Thr Glu Val Thr Ala Pro
    210                 215                 220

Pro Glu Asp Asn Pro Val Glu Asp Ser Gln Val Ile Val Glu Glu Val
225                 230                 235                 240

Ser Ile Phe Pro Val Glu Glu Gln Gln Glu Val Pro Pro Asp Thr
                245                 250                 255

<210> SEQ ID NO 2
<211> LENGTH: 3
<212> TYPE: PRT
<213> ORGANISM: Artificial Sequence
<220> FEATURE:
<223> OTHER INFORMATION: Synthetic Construct

<400> SEQUENCE: 2

Glu Pro Ala
1

<210> SEQ ID NO 3
<211> LENGTH: 4
<212> TYPE: PRT
<213> ORGANISM: Artificial Sequence
```

-continued

```
<220> FEATURE:
<223> OTHER INFORMATION: Synthetic Construct

<400> SEQUENCE: 3

Val Pro Pro Glu
1

<210> SEQ ID NO 4
<211> LENGTH: 3
<212> TYPE: PRT
<213> ORGANISM: Artificial Sequence
<220> FEATURE:
<223> OTHER INFORMATION: Synthetic Construct

<400> SEQUENCE: 4

Glu Pro His
1

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Glu Pro Glu
1

<210> SEQ ID NO 6
<211> LENGTH: 3
<212> TYPE: PRT
<213> ORGANISM: Artificial Sequence
<220> FEATURE:
<223> OTHER INFORMATION: Synthetic Construct

<400> SEQUENCE: 6

Val Pro Val
1

<210> SEQ ID NO 7
<211> LENGTH: 3
<212> TYPE: PRT
<213> ORGANISM: Artificial Sequence
<220> FEATURE:
<223> OTHER INFORMATION: Synthetic Construct

<400> SEQUENCE: 7

Glu Pro Gln
1

<210> SEQ ID NO 8
<211> LENGTH: 3
<212> TYPE: PRT
<213> ORGANISM: Artificial Sequence
<220> FEATURE:
<223> OTHER INFORMATION: Synthetic Construct

<400> SEQUENCE: 8

Gly Pro Thr
1

<210> SEQ ID NO 9
<211> LENGTH: 3
<212> TYPE: PRT
<213> ORGANISM: Artificial Sequence
<220> FEATURE:
```

```
<223> OTHER INFORMATION: Synthetic Construct

<400> SEQUENCE: 9

Asn Pro Asp
1

<210> SEQ ID NO 10
<211> LENGTH: 3
<212> TYPE: PRT
<213> ORGANISM: Artificial Sequence
<220> FEATURE:
<223> OTHER INFORMATION: Synthetic Construct

<400> SEQUENCE: 10

Glu Pro Val
1

<210> SEQ ID NO 11
<211> LENGTH: 3
<212> TYPE: PRT
<213> ORGANISM: Artificial Sequence
<220> FEATURE:
<223> OTHER INFORMATION: Synthetic Construct

<400> SEQUENCE: 11

Glu Pro Leu
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Construct

<400> SEQUENCE: 12

Ala Pro Pro Glu
1

<210> SEQ ID NO 13
<211> LENGTH: 3
<212> TYPE: PRT
<213> ORGANISM: Artificial Sequence
<220> FEATURE:
<223> OTHER INFORMATION: Synthetic Construct

<400> SEQUENCE: 13

Asn Pro Val
1

<210> SEQ ID NO 14
<211> LENGTH: 3
<212> TYPE: PRT
<213> ORGANISM: Artificial Sequence
<220> FEATURE:
<223> OTHER INFORMATION: Synthetic Construct

<400> SEQUENCE: 14

Phe Pro Val
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct
```

```
<400> SEQUENCE: 15

Val Pro Pro Asp
1

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Glu Pro Ala Val Pro Pro Glu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Val Pro Pro Glu Glu Ala Glu Pro His
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Glu Pro His Thr Glu Pro Glu
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Glu Pro Glu Glu Gln Val Pro Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Val Pro Val Glu Ala Glu Pro Gln
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 21

Gly Pro Thr Gly Glu Pro Gln
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Asn Pro Asp Ser Ser Glu Pro Val
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Ala Pro Pro Glu Asp Asn Pro Val
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic Construct

<400> SEQUENCE: 24

Phe Pro Val Glu Glu Gln Gln Glu Val Pro Pro Asp
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Asp Gly Pro Thr Gly Glu Pro Gln Gln Glu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Glu Gln Glu Asn Pro Asp Ser Ser Glu Pro Val
1               5                   10

<210> SEQ ID NO 27
<211> LENGTH: 10
<212> TYPE: PRT
```

-continued

```
<213> ORGANISM: Artificial Sequence
<220> FEATURE:
<223> OTHER INFORMATION: Synthetic Construct

<400> SEQUENCE: 27

Ala Pro Pro Glu Asp Asn Pro Val Glu Asp
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Glu Glu Gln Gln Glu Val Pro Pro Asp
1               5

<210> SEQ ID NO 29
<211> LENGTH: 22
<212> TYPE: PRT
<213> ORGANISM: Artificial Sequence
<220> FEATURE:
<223> OTHER INFORMATION: Synthetic Construct

<400> SEQUENCE: 29

Gly Glu Asp Leu Gln Gln Glu Asp Gly Pro Thr Gly Glu Pro Gln Gln
1               5                   10                  15

Glu Asp Asp Glu Phe Leu
            20

<210> SEQ ID NO 30
<211> LENGTH: 22
<212> TYPE: PRT
<213> ORGANISM: Artificial Sequence
<220> FEATURE:
<223> OTHER INFORMATION: Synthetic Construct

<400> SEQUENCE: 30

Asp Met Glu Glu Met Met Ser Glu Gln Glu Asn Pro Asp Ser Ser Glu
1               5                   10                  15

Pro Val Val Glu Asp Glu
            20

<210> SEQ ID NO 31
<211> LENGTH: 22
<212> TYPE: PRT
<213> ORGANISM: Artificial Sequence
<220> FEATURE:
<223> OTHER INFORMATION: Synthetic Construct

<400> SEQUENCE: 31

Asn Glu Gly Ile Glu Ile Thr Glu Val Thr Ala Pro Pro Glu Asp Asn
1               5                   10                  15

Pro Val Glu Asp Ser Gln
            20

<210> SEQ ID NO 32
<211> LENGTH: 23
<212> TYPE: PRT
<213> ORGANISM: Artificial Sequence
<220> FEATURE:
<223> OTHER INFORMATION: Synthetic Construct

<400> SEQUENCE: 32
```

-continued

```
Asp Ser Gln Val Ile Val Glu Glu Val Ser Ile Phe Pro Val Glu Glu
1               5                   10                  15

Gln Gln Glu Val Pro Pro Asp
            20
```